United States Patent

Oh et al.

[11] Patent Number: 5,858,306
[45] Date of Patent: Jan. 12, 1999

[54] MODIFIED NOBLE METAL CATALYST BASED CALORIMETRIC SENSOR AND METHOD

[75] Inventors: Seajin Oh; Jose Joseph, both of Palo Alto; Dao Duong, Fremont, all of Calif.; Neil J. Adams, Novi; Steven L. Plee, Brighton, both of Mich.

[73] Assignee: Motorola, Inc., Schaumburg, Ill.

[21] Appl. No.: 673,887

[22] Filed: Jul. 1, 1996

[51] Int. Cl.⁶ .......................... G01N 25/00; G01N 25/20; G01N 27/00; G01N 31/00
[52] U.S. Cl. .................. 422/51; 422/83; 422/96; 422/98
[58] Field of Search ................. 422/51, 83, 96, 422/98

[56] References Cited

U.S. PATENT DOCUMENTS 5,451,371  9/1995  Zanini-Fischer et al. ................. 422/51

FOREIGN PATENT DOCUMENTS 9800704  1/1988  WIPO ............................. G01N 25/00

OTHER PUBLICATIONS

"Detection of Methane/Butane Mixtures in Air by a Set of Two Microcalorimetric Sensors" by V. Sommer, R. Rongen, P. Tobias and D. Kohl from Sensors and Actuators (1992), published by Elsevier Sequoia, pp. 262–265.

"The Role of Catalysis in Solid–State Gas Sensors" by S. Gentry and T. Jones, from Sensors and Actuators10 (1986), published by Elsevier Sequoia, pp. 141–163.

*Primary Examiner*—Avis M. Davenport
*Attorney, Agent, or Firm*—Nicholas C. Hopman

[57] ABSTRACT

A modified noble metal catalyst based calorimetric sensor for sensing non-methane hydrocarbons in an automotive exhaust gas stream includes a first sensing element (105) with an output that provides a signal (111) indicative of a concentration of indicative of non-methane hydrocarbons, hydrogen ($H_2$), and carbon monoxide (CO). A compensating sensing element (107) has an output that provides a compensating signal (113) indicative of a concentration of hydrogen ($H_2$) and carbon monoxide (CO). A circuit for combining the signal and the compensating signal provides a combined signal indicative of a measure of non-methane hydrocarbons in the automotive exhaust gas stream.

12 Claims, 22 Drawing Sheets

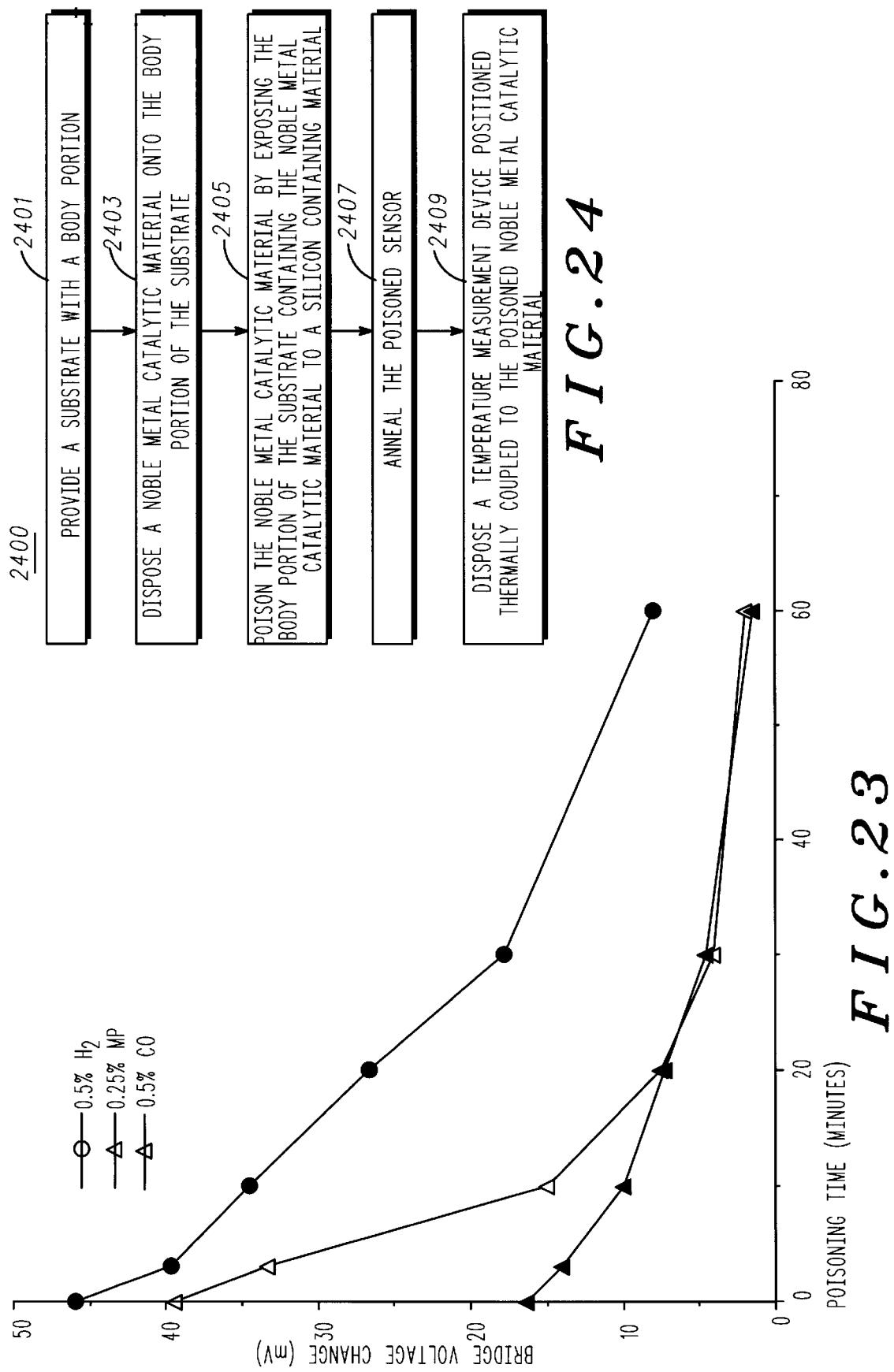

MODIFIED NOBLE METAL CATALYST BASED CALORIMETRIC SENSOR AND METHOD

FIELD OF THE INVENTION

This invention is generally directed to the field of sensors, and more particularly to calorimetric sensors based on noble metal catalysts.

BACKGROUND OF THE INVENTION

Calorimetric sensors are often employed to measure gas concentration of one gas or a combination of gases. Certain prior art calorimetric sensors are constructed using noble metals as catalysts to determine concentrations of certain gases, or groups of gases. Noble metal catalysts promote oxidation of a combustible gases, or gases to be measured. Oxidation reactions generate heat, which causes a rise in temperature proximate an area of the reaction. A resulting increase in temperature can be sensed, and used to indicate a concentration of the combustible gas or gases under measure.

As a practical matter, catalysts are rarely selectively reactive to a particular gas molecule. As a result, gases other than the selected one, or selected group, of interest can cause interference during a measurement process. Therefore, the achievement of a reasonable degree of gas molecule selectivity is a major technical hurdle to overcome in sensor design.

An example of gas interference can be seen in application of a hydrocarbon sensor located in an exhaust gas plenum of a vehicle. Hydrocarbon sensors are required to measure concentration of non-methane (or heavy) hydrocarbons in internal combustion engine exhaust gas streams in the presence of other combustible gases.

The need for employing hydrocarbon sensors in vehicular applications, particularly automotive vehicles, is driven by environmental emissions legislation that is regularly being changed to require lower and lower emissions of pollutants from vehicles—hydrocarbons included. In particular, the California Air Resources Board (CARB) is leading an effort with their LEV (Low Emission Vehicle) and ULEV (Ultra Low Emission Vehicle) standards and the accompanying OBDII (On-Board Diagnostics II) requirement. For a LEV, OBDII requires detection of changes in catalytic converter non-methane hydrocarbon conversion efficiency of the order of 1–2%. This corresponds to a requirement to detect changes in emitted non-methane hydrocarbons of tens of PPM (parts per million).

Internal combustion engines exhaust gases including hydrogen ($H_2$), carbon monoxide (CO), methane ($CH_4$), carbon dioxide ($CO_2$), non-methane hydrocarbons ($CH_x$), nitric oxide (NO), and water vapor ($H_2O$). Sensors that are currently available cannot selectively detect non-methane hydrocarbons ($CH_x$) in these engine exhaust gas streams. In hydrocarbon sensors using noble metals as a catalyst, it is very difficult to eliminate hydrogen ($H_2$) interference, when other combustible gases such as non-methane hydrocarbons have to be measured selectively.

What is needed is an improved non-methane hydrocarbon sensor that is less sensitive to interference from combustible gasses in the exhaust gas stream, other than non-methane hydrocarbons, particularly hydrogen ($H_2$)

BRIEF DESCRIPTION OF THE DRAWINGS

FIG. 23 shows a graph derived from an alternate sensing element constructed using an inactive GasTech model 62-0300 sensing element coated with a thick film coated sensing element of the controllably poisonable catalyst; and FIG. 24 is a flow chart showing a process for fabricating a poisoned noble metal based sensor in accordance with a method embodiment of the invention.

DETAILED DESCRIPTION OF A PREFERRED EMBODIMENT

A modified noble metal catalyst based calorimetric sensor is constructed using a noble metal catalyst that has been modified, or poisoned by another material, preferably silicon based. Whereas noble metal catalysts are ordinarily purposefully fabricated as pure as economically practical, poisoning is applied to shift the combustion temperature of various gasses constituent in a gas stream to be measured by the sensor. A temperature measurement device is positioned thermally coupled to the poisoned noble metal catalytic material. The temperature measurement device has output terminals that provide a signal with a magnitude indicative of a temperature proximate the thermal coupling. Preferably, the noble metal catalyst is either a platinum (Pt), palladium (Pd), or rhodium (Rh) material.

In an automotive internal combustion engine exhaust gas stream application, the sensor described above, in combination with another noble metal catalyst based sensor, can sense heavier (non-methane) hydrocarbons in the presence of interfering gasses including hydrogen ($H_2$), carbon monoxide (CO), methane ($CH_4$), carbon dioxide ($CO_2$), nitric oxide (NO), and water vapor ($H_2O$), which gasses are all present in the automotive exhaust gas stream. Note that the structure and methods described herein are useful outside of automotive applications.

Figure 1:
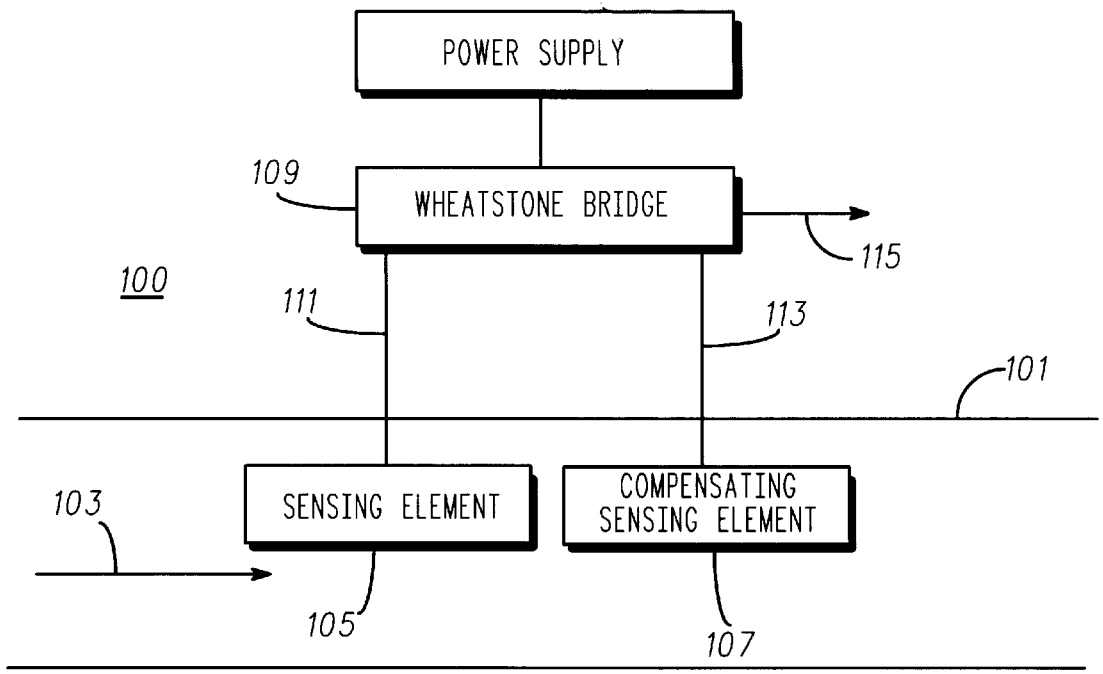
FIG. 1 is a schematic drawing showing a general configuration of a calorimetric sensor and measurement circuit in accordance with a preferred embodiment of the invention.

FIG. 1 is a schematic drawing showing a general configuration of a calorimetric sensor 100 in accordance with a preferred embodiment of the invention for an automotive application. The sensor 100, is disposed in an exhaust gas plenum 101 and measures non-methane hydrocarbons in the presence of other exhaust gases including hydrogen ($H_2$), carbon monoxide (CO), carbon dioxide ($CO_2$), methane ($CH_4$), nitric oxide (NO), and water vapor ($H_2O$) all present in an automotive exhaust gas stream 103. In the automotive application a preferred configuration for the sensor comprises two sensing elements. Essentially, a first sensing element 105 provides a signal 111 indicative of hydrocarbons ($CH_x$) with the exception of methane ($CH_4$), and the other above-identified coexisting gasses in the exhaust gas stream 103. A compensating sensing element 107 provides a compensating signal 113 indicative of a concentration of only the coexisting gasses in the exhaust gas stream 103, also with the exception of methane ($CH_4$). For the purpose of signal measurement these sensing elements 105 and 107 are configured in a Wheatstone bridge measurement circuit 109, however, other signal measurement techniques may be used. The Wheatstone bridge circuit 109 combines the signals 111 and 113 and provides a combined signal 115 indicative of a measure of non-methane hydrocarbons in the exhaust gas stream 103.

When the calorimetric sensor 100 operates in combustible gases, an onset of combustion on a sensing element depends on the sensing element's temperature and a catalyst composition on that sensing element. When a highly active catalyst is used, hydrogen ($H_2$) and carbon monoxide (CO) are oxidized at relatively low temperatures. Most hydrocarbons, but not methane ($CH_4$), are oxidized at relatively intermediate temperatures and methane ($CH_4$) is oxidized at relatively high temperatures. If a less active catalyst is used, combustion only occurs at relatively high temperatures, and thus the temperature of onset of combustion, or light-off temperature of the catalyst, is shifted to relatively higher temperatures. Note that the light-off temperature of the catalyst is a temperature above which combustion/oxidation occurs for a particular gas on a particular catalyst. A magnitude of this temperature shift is determined by the decrease in activity of the catalyst. It is desirable to raise the light-off temperature of the catalyst for certain gases so that the catalyst can be operated at a temperature that is below the light-off temperatures for certain gases, but above those for other gases. Thus the catalyst is rendered selective to those gases whose light-off temperatures are below the operating temperature. One way of decreasing the catalytic activity, or raising the light-off temperature of the catalyst for certain gases is to poison the catalyst. Ordinarily, great care is taken in producing pure (non-contaminated) noble metal based sensors. Here the noble metal catalyst is intentionally modified or poisoned, preferably with a silicon based material. For instance a hexamethyldisilazane (HMDS) material, or any other silicon-containing metal-organic material can be used.

Figure 2:
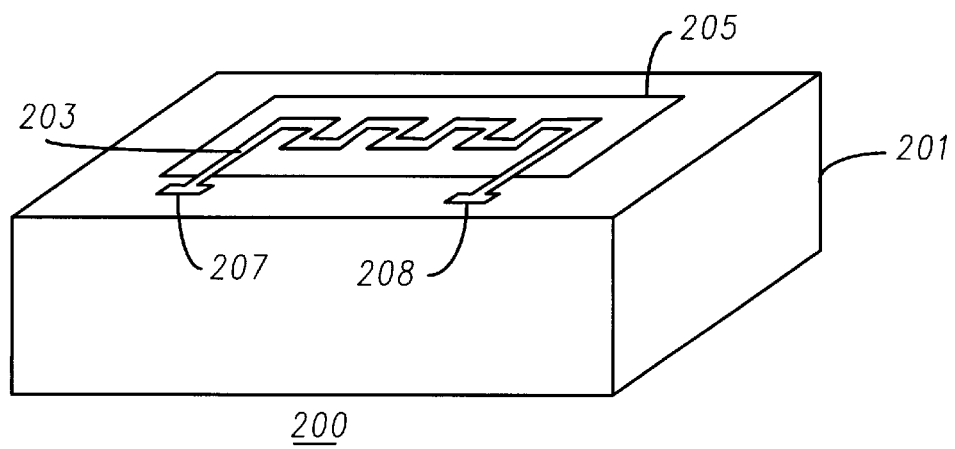
FIG. 2 is a mechanical drawing showing construction details of a planar architecture modified noble metal catalyst based calorimetric sensor.

A planar architecture sensing element (representing sensing element 105 in FIG. 1) is illustrated in FIG. 2. Note that different architectures are possible as long as the relationship between key sensing elements described below is maintained. A substrate, or carrier, 201 can be constructed using various materials. In one embodiment, the substrate 201 is constructed of a ceramic material. A poisoned noble metal catalytic material 205 is disposed onto a surface of the substrate 201, and a temperature measurement device 203 is disposed positioned thermally coupled to the poisoned noble metal catalytic material 205. Note that the temperature measurement device 203 could be disposed first and then the poisoned noble metal catalytic material 205 disposed on top of it—they simply have to be thermally coupled as efficiently as practical. The temperature measurement device 203, has output terminals 207 and 208 that provide a signal having a magnitude indicative of a temperature proximate the thermal coupling. As just-mentioned, sensing elements 203 and 205 may be oriented in a different configuration, as long as there is a thermal coupling between them. For example in an alternative architecture commonly referred to as a bead-type architecture, a catalyst is formed in a bead-type geometry surrounding a wire, and the wire is used as the temperature sensing element. Also, the poisoned noble metal catalytic material can be dispersed through (essentially infused into) the body portion of the substrate, or carrier. Test results presented below indicate that this arrangement can yield favorable results. Also, for optimal performance, the sensing elements should be controlled by the bridge circuit 109 or other equivalent circuitry to operate at a temperature above 200° C.

To prove out the effectiveness of modifying, or poisoning a (relatively pure) noble metal based sensor for detecting non-methane hydrocarbons ($CH_x$), commercial sensors from EEV (English Electric Valve, Waterhouse Lane, Chelmsford, Essex) (model VQ25) and GasTech 8407 Central Avenue, Newark, Calif. (model 62-0300), were used. Each of these sensors include a sensing element with a platinum (Pt) catalyst and were poisoned with hexamethyldisilazane (HMDS) vapor under various conditions. In the case of the model VQ25 EEV, this sensor has the catalyst distributed from the bead surface center while the catalyst of the model 62-0300 GasTech bead-type sensor is segregated near the surface.

After poisoning, these sensing elements were exposed to a measured concentration of methylpropene (MP) and ethene, selected to represent non-methane hydrocarbons, in the presence of the expected concentrations of hydrogen ($H_2$), carbon monoxide (CO), methane ($CH_4$), carbon dioxide ($CO_2$), nitric oxide (NO), and water vapor ($H_2O$) all typically present in an engine exhaust gas stream. The test results are shown later. Methylpropene (MP) and ethene were selected as targeted non-methane hydrocarbons because they are among the major non-methane hydrocarbon gases in a combustion engine exhaust gas stream.

To poison the platinum (Pt) catalyst of the sensing element of the model VQ25 EEV and model 62-0300 GasTech bead-type sensors, the powered sensing elements were exposed to a gas flow carrying hexamethyldisilazane (HMDS) vapor. The poisoning process consisted of two steps: exposure to hexamethyldisilazane (HMDS) vapor for a particular period, and annealing of the sensors at the same temperature for the same period without hexamethyldisilazane (HMDS) vapor.

A level of poisoning was controlled by the hexamethyldisilazane (HMDS) concentration, the poisoning time, and the temperature of the sensing element. The hexamethyldisilazane (HMDS) vapor was supplied by bubbling nitrogen ($N_2$) through a pure hexamethyldisilazane (HMDS) solution, and the hexamethyldisilazane (HMDS) concentration was controlled by the flow of the nitrogen ($N_2$) through a bubbler. Note that vapor pressure of hexamethyldisilazane (HMDS) is approximately 3% at room temperature. Total flow rate was 2,000 sccm (standard cubic centimeters per minute).

An example calorimetric sensor fabrication process flow chart is shown in FIG. 24. The process 2400 commences at a step 2401 where a substrate is provided including a body portion. As mentioned in reference to FIG. 2 earlier, the substrate is preferably constructed of a ceramic material. Also, the substrate can take on any geometric form convenient for processing. Next, in step 2403 a noble metal catalytic material is disposed onto the body portion of the substrate. The noble metal material is preferably platinum (Pt), palladium (Pd), or rhodium (Rh) based, but any noble metal material could be substituted. One technique to dispose the noble metal material is to first prepare a slurry including silica power, alumina powder, and $Al(NO_3)_3$ $9H_2O$ as catalyst carriers, $H_2PtCl_6$ as a noble metal based controllably poisonable catalyst material, and some surfactant agents. The slurry is then applied to the body portion of the substrate.

Next, in step 2405, the noble metal based controllably poisonable catalyst material is poisoned by exposing the body portion of the substrate containing the noble metal catalytic material to a silicon containing material. Preferably, the poisoning step 2405 includes heating the substrate to a predetermined temperature prior to exposing the body portion of the substrate containing the noble metal catalytic material to the silicon containing material. This step 2405 is executed for a fixed period of time.

Then, in step 2407, the poisoned sensor is annealed. Preferably, the annealing step 2407 of the poisoned sensor is executed for the fixed period of time associated with the step of poisoning.

To complete the sensor a temperature measurement device is disposed positioned thermally coupled to the poisoned noble metal catalytic material.

The model VQ25 EEV sensing element was poisoned by 0.3% hexamethyldisilazane (HMDS) vapor, and the model 62-0300 GasTech bead-type sensing element was poisoned by 0.03% hexamethyldisilazane (HMDS) vapor. Since the catalyst of the model 62-0300 GasTech bead-type sensing element is segregated near the sensor surface, it can be more easily poisoned than the VQ25 EEV sensing element. The maximum poisoning time was 60 minutes for the model VQ25 EEV sensor. The temperature of the sensing element was controlled by the voltage applied to the sensing element. The sensing elements were poisoned at two different temperatures: 430° C. (Celsius), and 630° C.

Alternate sensing elements were made by coating non-catalytic model 62-0300 GasTech bead-type sensing elements with a controllably poisoned catalyst to fabricate a diffused (or nonsegregated) catalyst sensor. Essentially, the non-catalytic model 62-0300 GasTech sensing element was not completely manufactured so that the controllably poisoned catalyst described below could be evaluated. The controllably poisonable catalyst consisted of silica power, alumina powder, and $Al(NO_3)_3$ $9H_2O$ as catalyst carriers, $H_2PtCl_6$ as a catalyst, and some surfactant agents (such as "IGEPAL CO-990", from Aldrich, Inc. 1001 West Saint Paul Av. Milwaukee, Wis. 53233) but may consist of other materials selected to give the same results. The catalyst is designed to be capable of being controllably poisoned, to achieve the required selectivity to combustible gases, and will be referred to below as a controllably poisonable catalyst.

Because the sensing elements provided by model VQ25 EEV and model 62-0300 GasTech were designed to measure high-concentration gases, the concentrations of test gases in the study were approximately 10 to 100 times higher than in actual automotive exhaust gas concentrations. The methylpropene (MP) concentration ranged from 400 to 2,500 PPM (parts per million), and the ethene concentration ranged from 1,000 to 4,000 PPM.

As mentioned earlier, selective measurements of methylpropene (MP) and ethene were conducted in the presence of hydrogen ($H_2$), carbon monoxide (CO), methane ($CH_4$), carbon dioxide ($CO_2$), nitric oxide (NO), and water vapor ($H_2O$).

The water ($H_2O$) vapor was supplied by bubbling nitrogen ($N_2$) through deionized water. The experiments were conducted at a 2,000-sccm total flow rate. Oxygen concentration was 6.5%, which was sufficient to burn the combustible gases in the gas mixtures.

Figure 3:
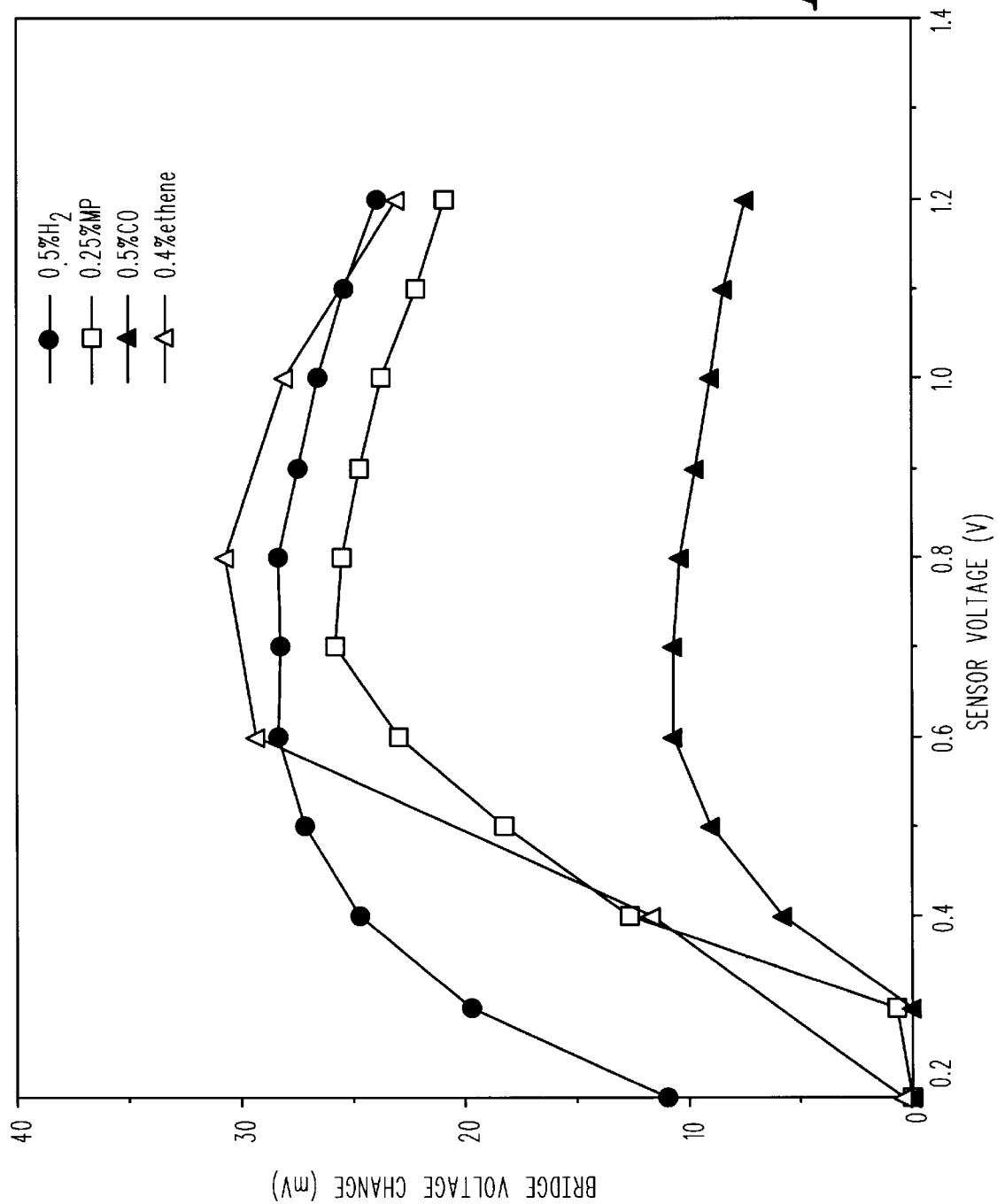
FIG. 3 is a graph illustrating an unpoisoned model VQ25 English Electric Valve sensor's response to various gasses expected in an automotive exhaust system.

For baseline reference purposes, FIG. 3 is a graph illustrating an unpoisoned model VQ25 EEV sensing element's response to various gasses expected in an automotive exhaust system. Note that in FIG. 3, and later described FIGS. 4–22, and 23, the Y-axis represents an output voltage of a Wheatstone Bridge circuit used to test two sensing elements as a sensor pair as shown in FIG. 1. In FIG. 3 the signal changes of the unpoisoned model VQ25 EEV sensing element to 0.5% hydrogen ($H_2$), 0.5% carbon monoxide (CO), 0.25% methylpropene (MP), and 0.4% ethene are shown as a function of the voltage applied to the sensing element which is related to the sensing element's operating temperature. More specifically, a voltage is applied to the element under evaluation to establish a particular operating temperature of the element through heating. Since the sensing elements are essentially resistive in nature, current flowing through the sensing elements induced by the voltage applied is dissipated in the form of heat. Returning to FIG. 3, the signal rapidly increased proximate an onset voltage, which was below 0.3 volts, and reached a maximum in the range 0.6 to 0.8 volts, followed by a slow decrease with further increase in the sensing element operating voltage (and hence temperature of the sensing element).

Figure 4:
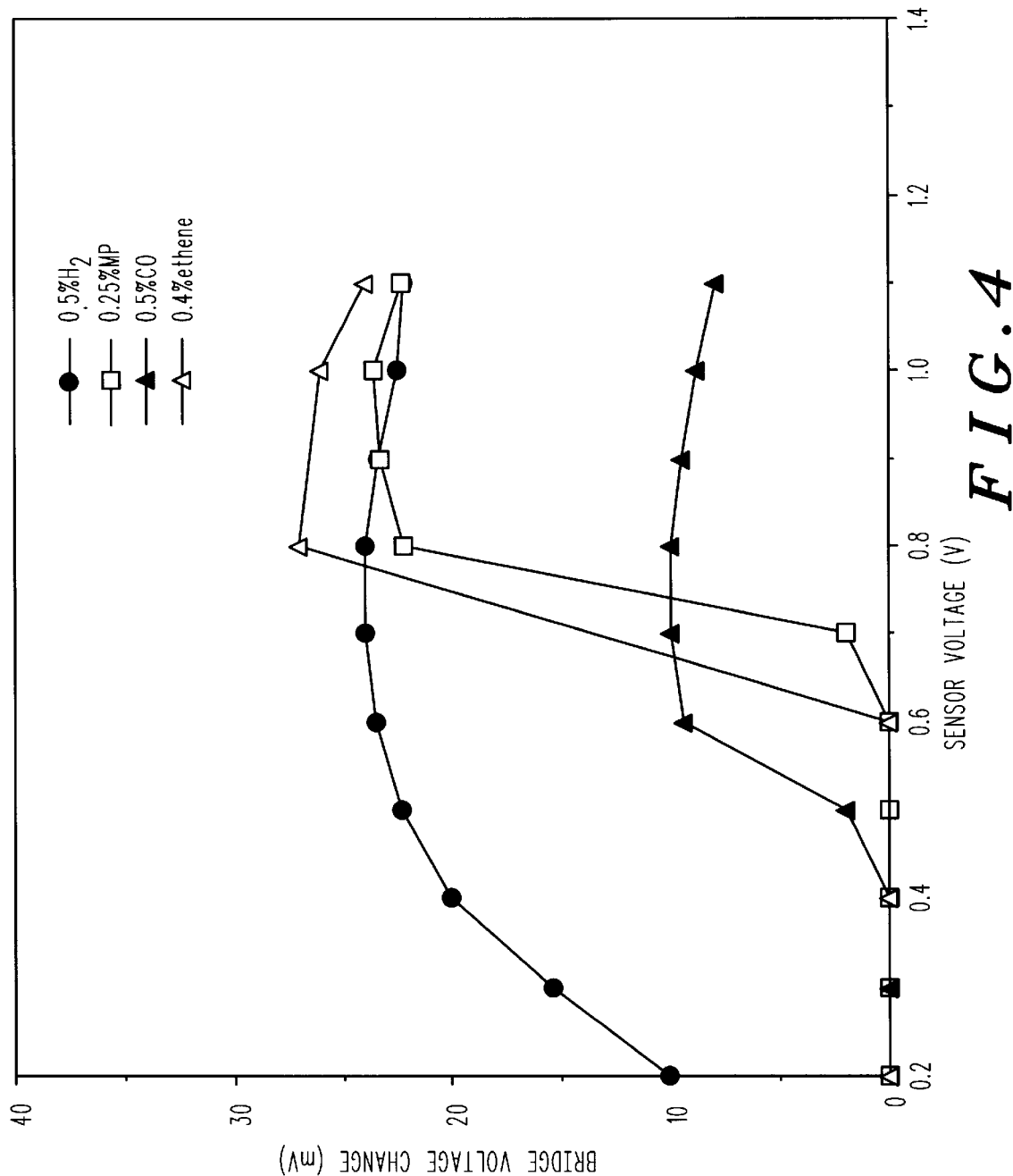
FIG. 4 is a graph showing a lightly poisoned model VQ25 English Electric Valve sensor's response to various gasses expected in an automotive exhaust system.

FIG. 4 is a graph illustrating a lightly poisoned model VQ25 EEV sensing element's response to various gasses expected in an automotive exhaust system. In particular, the model VQ25 EEV sensing element was poisoned at an applied bias of 1 volt which is equivalent to an operating temperature of 430° C., for approximately 30 minutes by 0.3% hexamethyldisilazane (HMDS) vapor.

Figure 5:
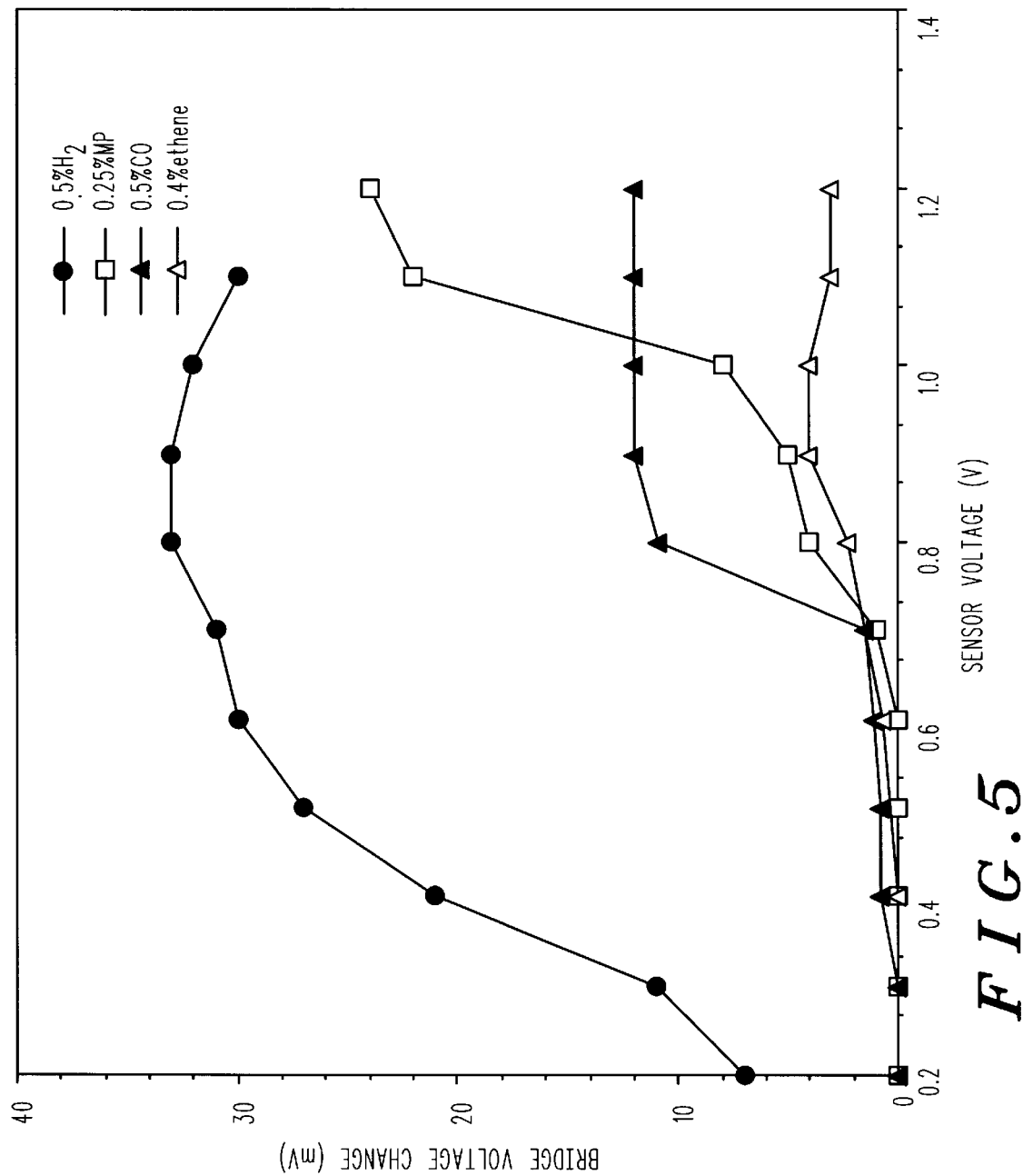
FIG. 5 is a graph illustrating a heavily poisoned model VQ25 English Electric Valve sensor's response to various gasses expected in an automotive exhaust system.

FIG. 5 is a graph illustrating a heavily poisoned model VQ25 EEV sensing element's response to various gasses expected in an automotive exhaust system. In particular, the model VQ25 EEV sensor was poisoned at an applied bias of 1.4 volts, which is equivalent to a sensing element operating temperature of about 630° C., for about one hour by 0.3% hexamethyldisilazane (HMDS) vapor.

When the model VQ25 EEV sensing element was poisoned by the hexamethyldisilazane (HMDS) vapor, the onset of combustion of hydrogen ($H_2$) still occurred at the same temperature, but the curves for methylpropene (MP) and ethene were shifted to the right, showing that the onset temperature of their combustion increased, as illustrated in FIGS. 4 and 5. The carbon monoxide (CO) curve was shifted to the right to some extent, but the degree of shift was smaller than that of methylpropene (MP) or ethene. The signal loss of ethene was greater, as shown in FIG. 5 where the heavily poisoned sensing element was not very sensitive to ethene at an applied bias of 1.2 volts, which is equivalent to a sensing element operating temperature of about 600° C.

If the poisoned noble metal catalyst based sensing elements operated at an applied bias of 0.9 volts, corresponding to approximately a 400° C. operating temperature, the lightly poisoned sensing element, as shown in FIG. 4, measured hydrogen ($H_2$), carbon monoxide (CO), methylpropene (MP), and ethene, while the heavily poisoned sensing element, as shown in FIG. 5, measured only the hydrogen ($H_2$) and carbon monoxide (CO). If the sensing elements were a matched pair, that is, they had exactly the same thermal mass, and hence exactly the same responses to hydrogen ($H_2$) and carbon monoxide (CO), subtraction of the latter signal from the former would give a sum of methylpropene (MP) and ethene concentrations. Alternatively, any thermal mismatch of the pair of sensing elements can be compensated for by calibration of the sensing elements, and the same result achieved. Calibration of the sensing elements can be accomplished at the time of manufacture. For instance the Wheatstone Bridge circuit can be trimmed to compensate for sensing element component mismatch.

When the sensing element is deployed in an actual application, its operating voltage (bias) should be kept lower than the poisoning voltage; otherwise, testing revealed that the sensing element's sensitivity to methylpropene (MP) and ethene was slowly recovered. Note that it is convenient to bias the sensing elements in the actual application to regulate the sensing element's operating temperature to maintain optimal performance. When the sensing element was poisoned at an applied bias of 1.4 volts, which is equivalent to a sensing element operating temperature of about 630° C., the operating voltage suitable for detecting methylpropene (MP) and ethene ranged from 0.8 to 1.2 volts (equivalent to an operating temperature range of approximately 380° C. to 600° C.). Higher-temperature poisoning has been shown to shift the response curves further to the right on the graph, thereby expanding the upper limit of the operating voltage or temperature.

Next, sensing elements modified by various levels of poisoning are combined and exposed to methylpropene (MP) and ethene, selected to represent non-methane hydrocarbons, in the presence of the background gasses expected in an automotive exhaust system.

A preferred sensor configuration comprises one heavily poisoned sensing element and one lightly poisoned (compensating or reference) sensing element configured in a Wheatstone bridge measurement circuit as shown in FIG. 1. In other words a concentration of poisoning of the poisoned noble metal catalytic material of the compensating sensing element is less than a concentration of poisoning of the poisoned noble metal catalytic material associated with the other sensing element. This combined sensing element configuration will be referred to as a sensor pair below. The lightly poisoned sensing element is used because an unpoisoned sensing element operating at the optimal temperature for the heavily poisoned sensing element has passed its point of peak selectivity. Furthermore, by lightly poisoning the second (reference) sensing element it is not only more selective of the gas species of interest but also is less sensitive to temperature variations. Also, an unpoisoned sensing element is sensitive to methane ($CH_4$) which will interfere with measurement of methylpropene (MP) and other non-methane hydrocarbons.

Figure 6:
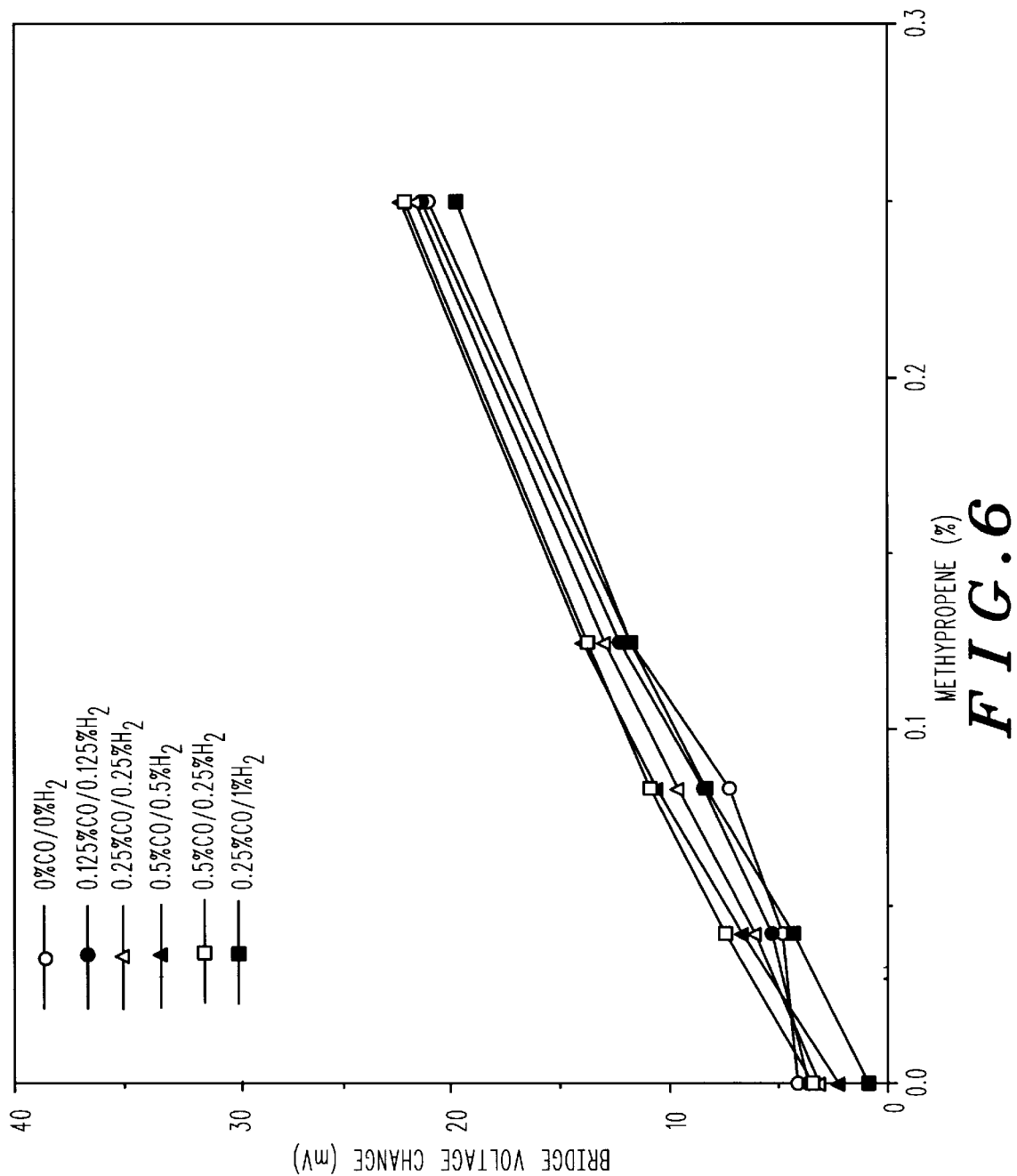
FIG. 6 is a graph illustrating measurement of methylpropene (MP) in the presence of different concentrations of hydrogen ($H_2$) and carbon monoxide (CO) using a lightly poisoned sensor and a heavily poisoned sensor in a Wheatstone bridge configuration.
Figure 7:
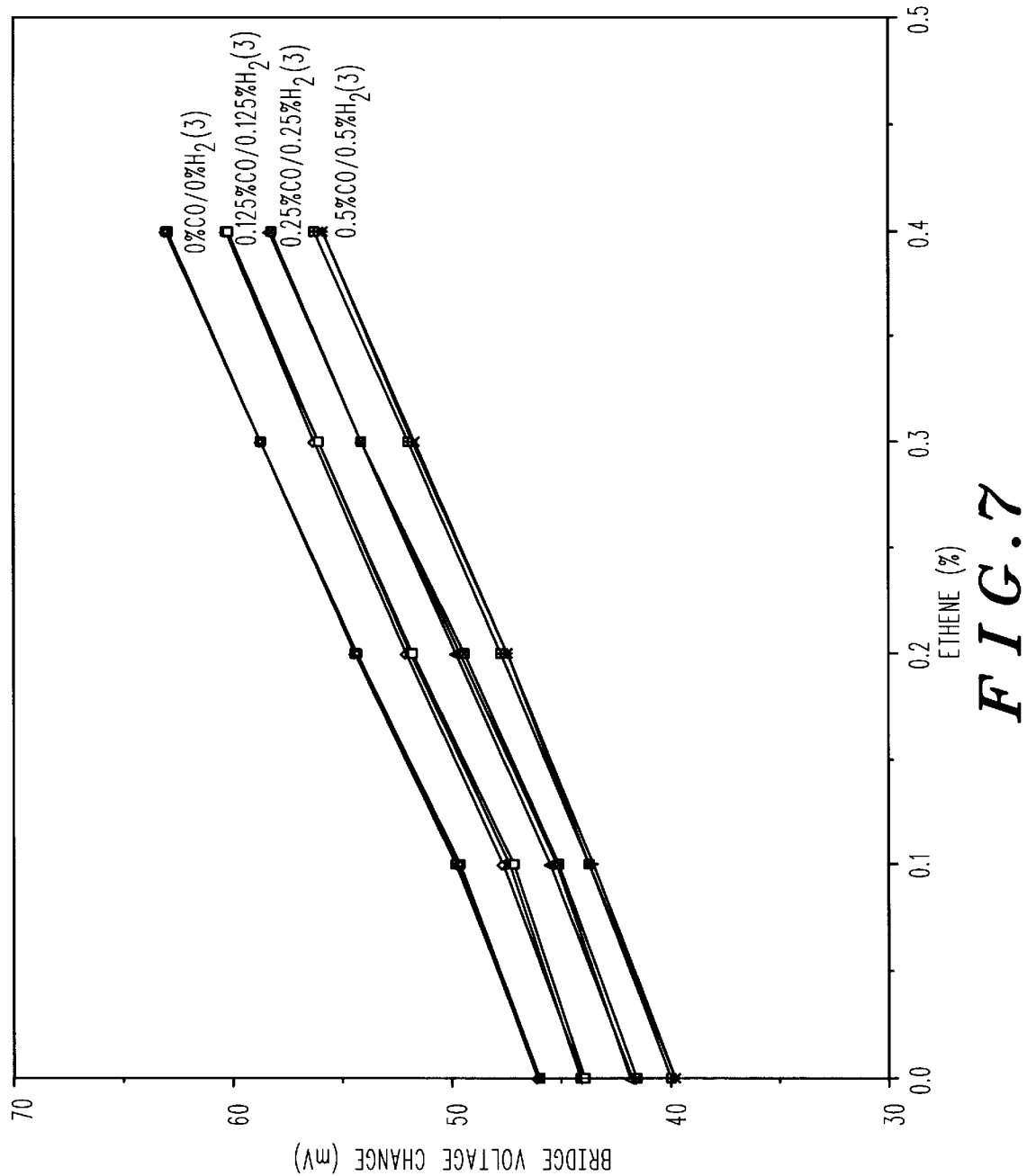
FIG. 7 is a graph showing measurement of ethene in the presence of hydrogen ($H_2$) and carbon monoxide (CO) using a lightly poisoned sensor and a heavily poisoned sensor arranged in a Wheatstone bridge configuration, where the ratio of hydrogen ($H_2$) to carbon monoxide (CO) is held constant while varying ethene in absolute magnitude over a range of zero to 0.5%.
Figure 8:
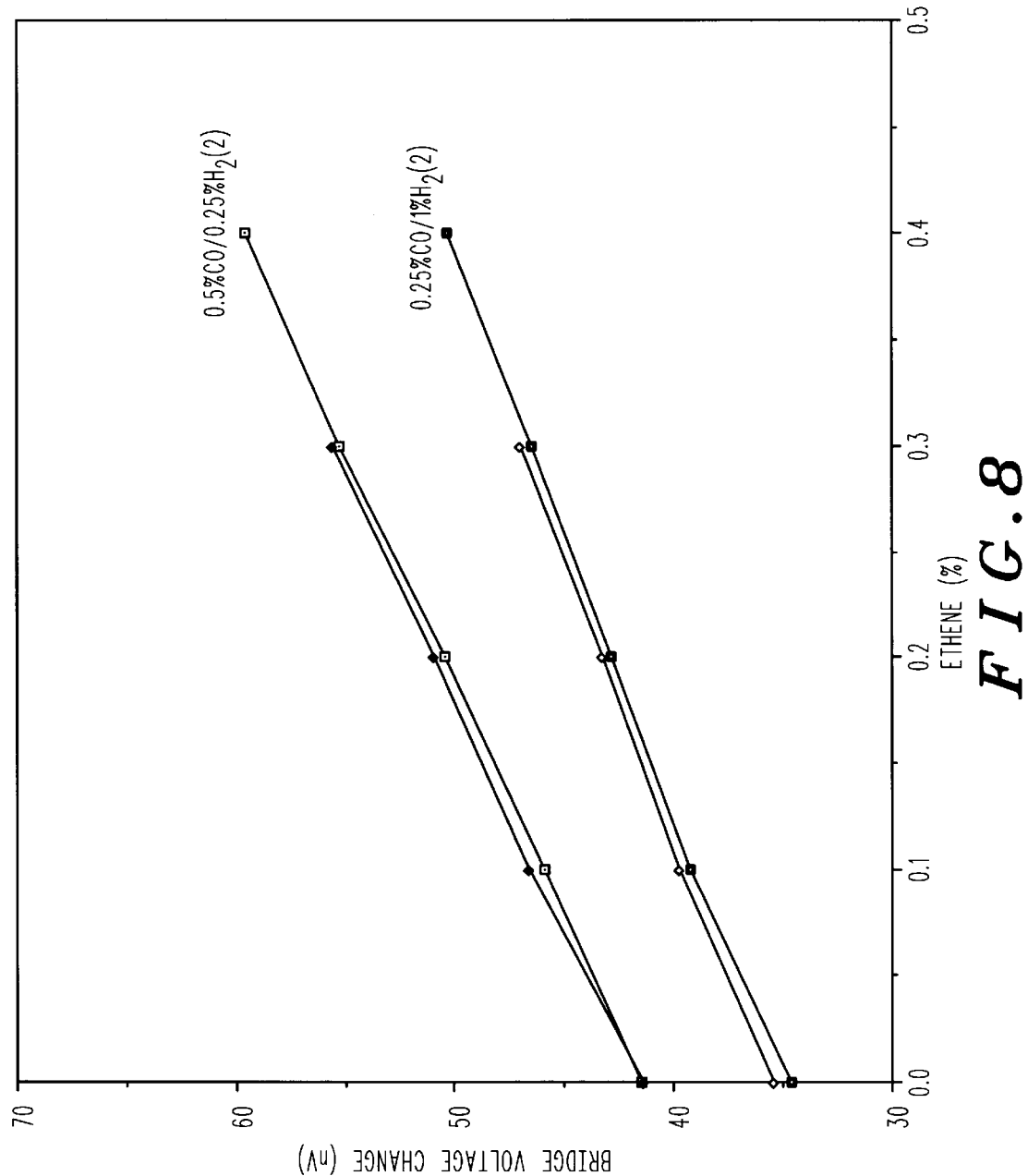
FIG. 8 is a graph illustrating measurement of ethene in the presence of hydrogen ($H_2$) and carbon monoxide (CO) using a lightly poisoned sensor and a heavily poisoned sensor in a Wheatstone bridge configuration, where the ratio of hydrogen ($H_2$) to carbon monoxide (CO) is varied.

Results of the measurements of methylpropene (MP) and ethene in the presence of various concentrations of hydrogen ($H_2$), and carbon monoxide (CO) are shown in FIGS. 6, 7, and 8.

Specifically, FIG. 6 shows a graph illustrating measurement of methylpropene (MP) in the presence of hydrogen ($H_2$) and carbon monoxide (CO) using a lightly poisoned sensing element and a heavily poisoned sensing element applied in a Wheatstone bridge configuration described earlier. Various concentrations of hydrogen ($H_2$) and carbon monoxide (CO) did not affect the linearity of the measurements. Measurements at low concentrations were not reproducible because of the low sensitivity caused by the size (thermal mass) of the sensing elements used here, but response in the high concentrations was linear to the non-methane hydrocarbon concentrations.

An absolute magnitude of the signal shifted, when the hydrogen ($H_2$) and carbon monoxide (CO) concentrations were varied. This shift is due to the thermal mass mismatch of the two sensing elements which causes a difference in the responses. As the subtraction method (via the Wheatstone bridge configuration) was used, good matching of the sensing element pair to the background signals by hydrogen ($H_2$) and carbon monoxide (CO) was crucial to the measurement of non-methane hydrocarbons.

FIG. 7 is a graph showing measurement of ethene in the presence of hydrogen ($H_2$) and carbon monoxide (CO), where the ratio of hydrogen ($H_2$) to carbon monoxide (CO)

is held constant while varying ethene in absolute magnitude over a range of zero to 0.5%.

FIG. 8 is a graph illustrating measurement of ethene in the presence of hydrogen ($H_2$) and carbon monoxide (CO), where the ratio of hydrogen ($H_2$) to carbon monoxide (CO) is varied.

If the sensing element pair were matched better, or alternatively the thermal mismatch of the sensing element pair were compensated for by calibration of the sensing elements, the curves in FIGS. 7 and 8 would overlap to form a single curve. While the curves for methylpropene (MP) measurement shown in FIG. 6 appear to be grouped they are not ideal for accurate measurement because their response is not identical. This can be remedied through a calibration procedure during the sensing element's manufacturing process. The sensing element pair used for ethene measurement was much more mismatched, and thus the curves show an orderly shift with the variation of carbon monoxide (CO) and hydrogen ($H_2$) concentrations. The model VQ25 EEV sensors were not made by a batch process; thus, the sensing element pair were not well matched, which resulted in the different levels of poisoning. Well-matched sensing element pairs can be produced only through batch fabrication when manufacturing tolerances can be well controlled.

Figure 9:
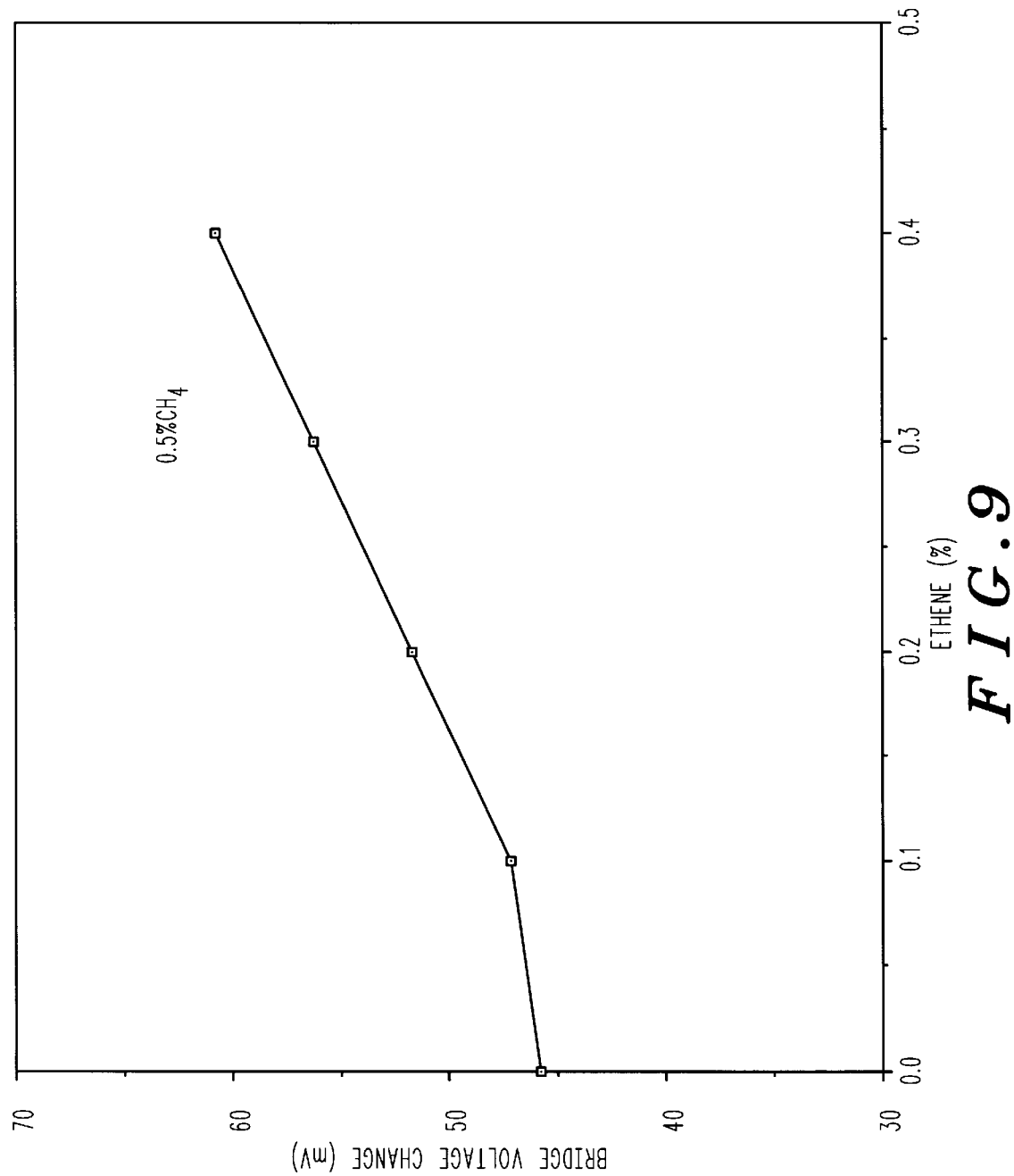
FIG. 9 is a graph showing measurement of ethene in the presence of methane ($CH_4$), where methane ($CH_4$) is held at 0.5% while ethene concentration is varied from 0% to 0.4%.
Figure 10:
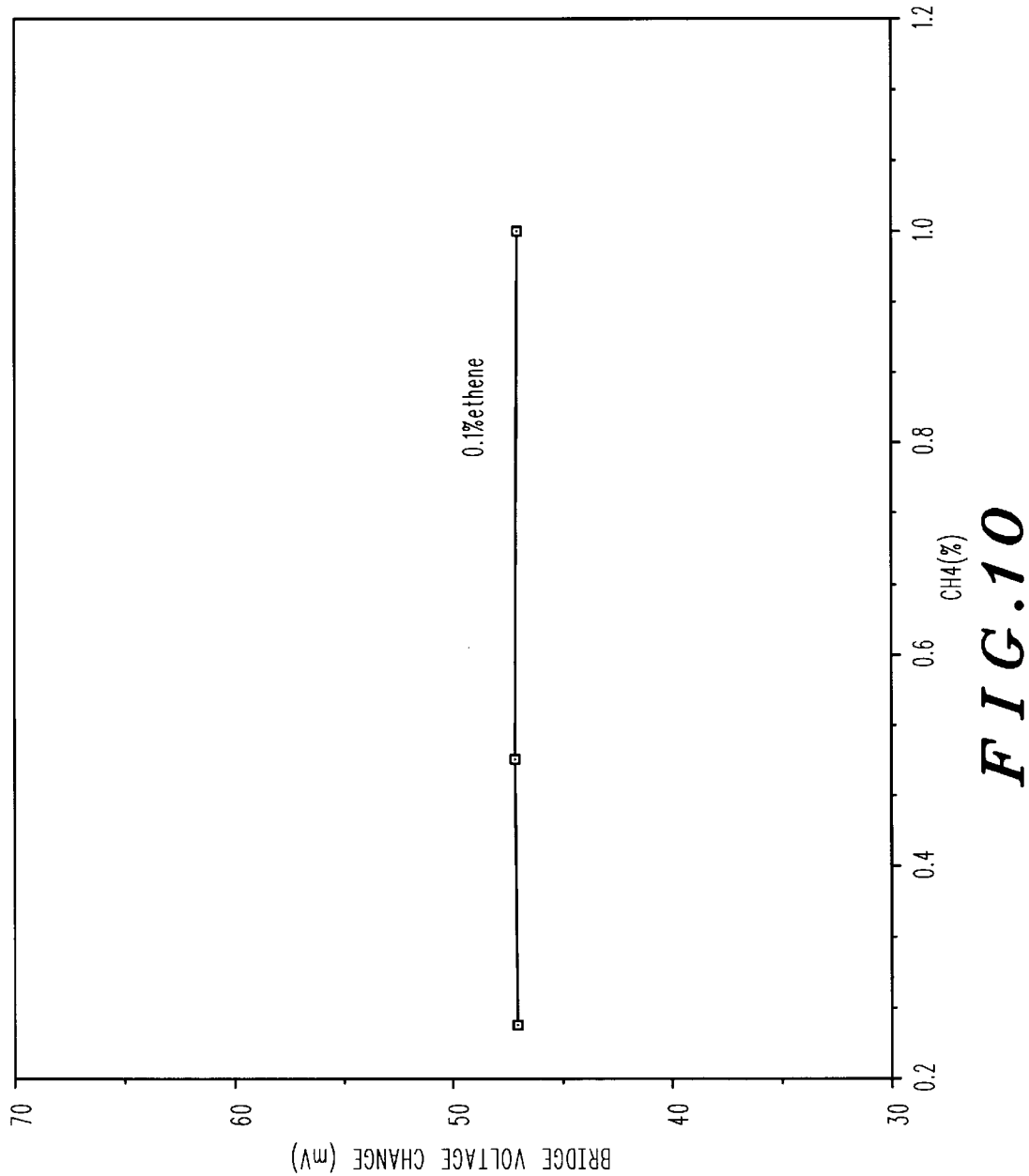
FIG. 10 is a graph illustrating measurement of ethene in the presence of methane ($CH_4$), where the methane ($CH_4$) concentration varied between 0.25% to 1%, and the ethene concentration is held at a constant 0.1%.

Next, methane ($CH_4$) response of the sensing element pair is evaluated. FIG. 9 shows a graph of ethene in the presence of methane ($CH_4$), where methane ($CH_4$) is held at 0.5% while ethene concentration is varied from 0% to 0.4%, and FIG. 10 is a graph illustrating measurement of ethene in the presence of methane ($CH_4$), where the methane ($CH_4$) concentration varied between 0.25% to 1%, and the ethene concentration is held at a constant 0.1%.

The sensing element pair responded linearly to ethene concentration from 0.1 to 0.4% in the presence of 0.5% methane ($CH_4$), as shown in FIG. 9. FIG. 10 is a graph illustrating measurement of ethene in the presence of methane ($CH_4$), where the methane ($CH_4$) concentration varied between 0.25% to 1%, and the ethene concentration is held at a constant 0.1%. The signal in the 0.1% ethene concentration was not changed even though methane ($CH_4$) concentration is varied from 0.25 to 1%. In view of the results presented in FIGS. 9 and 10, the presence of methane ($CH_4$) did not interfere with the ethene measurement.

Next, carbon dioxide ($CO_2$) and water ($H_2O$) vapor interference of the sensor pair is evaluated.

Figure 11:
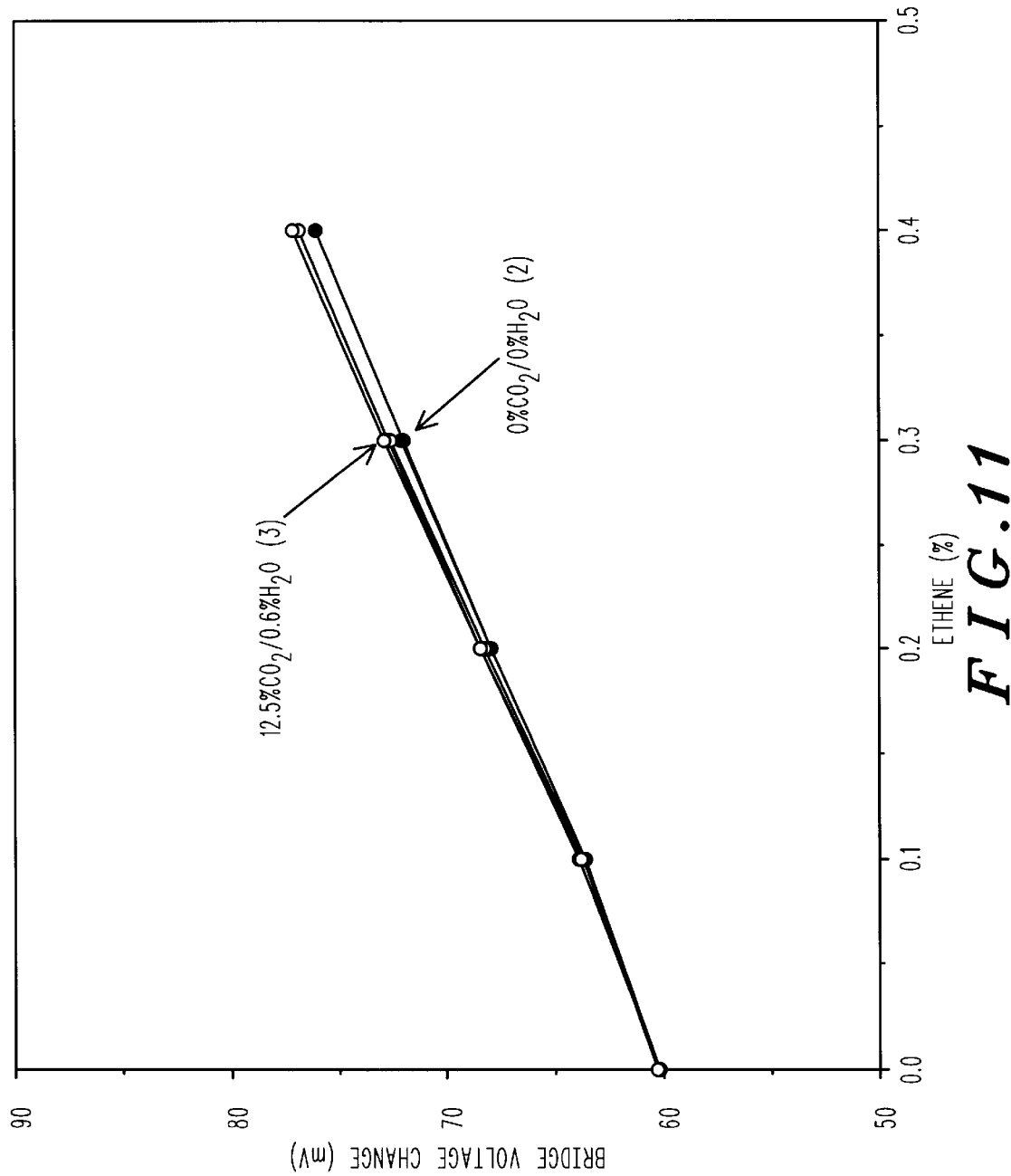
FIG. 11 is a graph showing measurement of ethene in the presence of carbon dioxide ($CO_2$) and water ($H_2O$) vapor, where carbon dioxide ($CO_2$) and water ($H_2O$) vapor were kept constant while ethene is varied from 0% to 0.4%.

FIG. 11 is a graph showing measurement of ethene in the presence of carbon dioxide ($CO_2$) and water ($H_2O$) vapor, where carbon dioxide ($CO_2$) and water ($H_2O$) vapor were kept constant while ethene is varied from 0% to 0.4%. The sensing element pair yielded a relatively linear response to ethene from 0.1 to 0.4% in the presence of carbon dioxide ($CO_2$) and water ($H_2O$) vapor, and the responses were very close to those obtained in the absence of carbon dioxide ($CO_2$) and water ($H_2O$) vapor.

Figure 12:
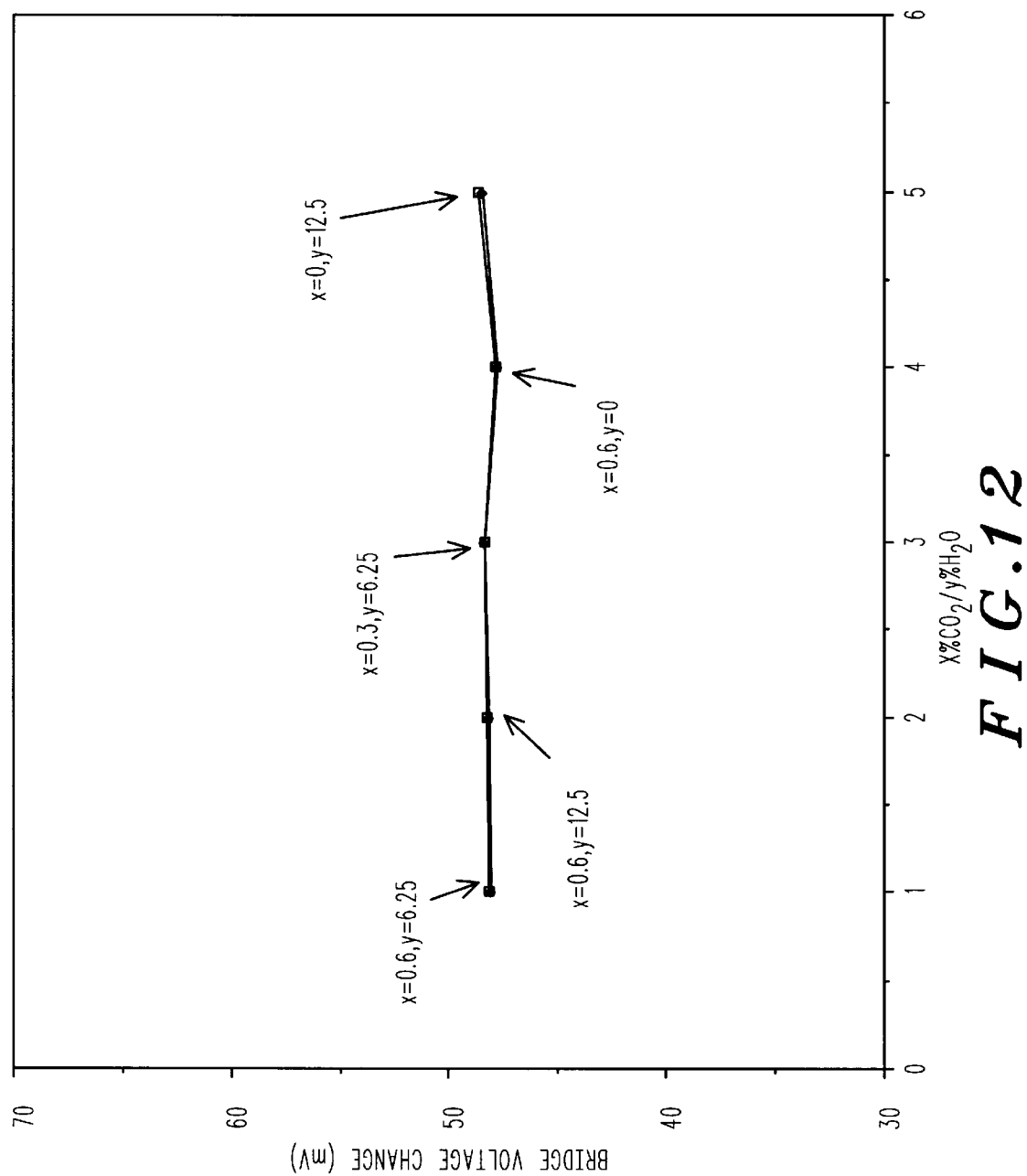
FIG. 12 is a graph illustrating the effect of carbon dioxide ($CO_2$) and water ($H_2O$) vapor concentrations on the measurement of 0.2% ethene.

FIG. 12 is a graph illustrating the effect of carbon dioxide ($CO_2$) and water ($H_2O$) vapor concentrations on the measurement of 0.2% ethene. The signal magnitude was not significantly affected by the change of carbon dioxide ($CO_2$) and water ($H_2O$) vapor concentrations.

Next, results of ethene measurement in the different nitric oxide (NO) concentrations are evaluated for the sensing element pair.

Figure 13:
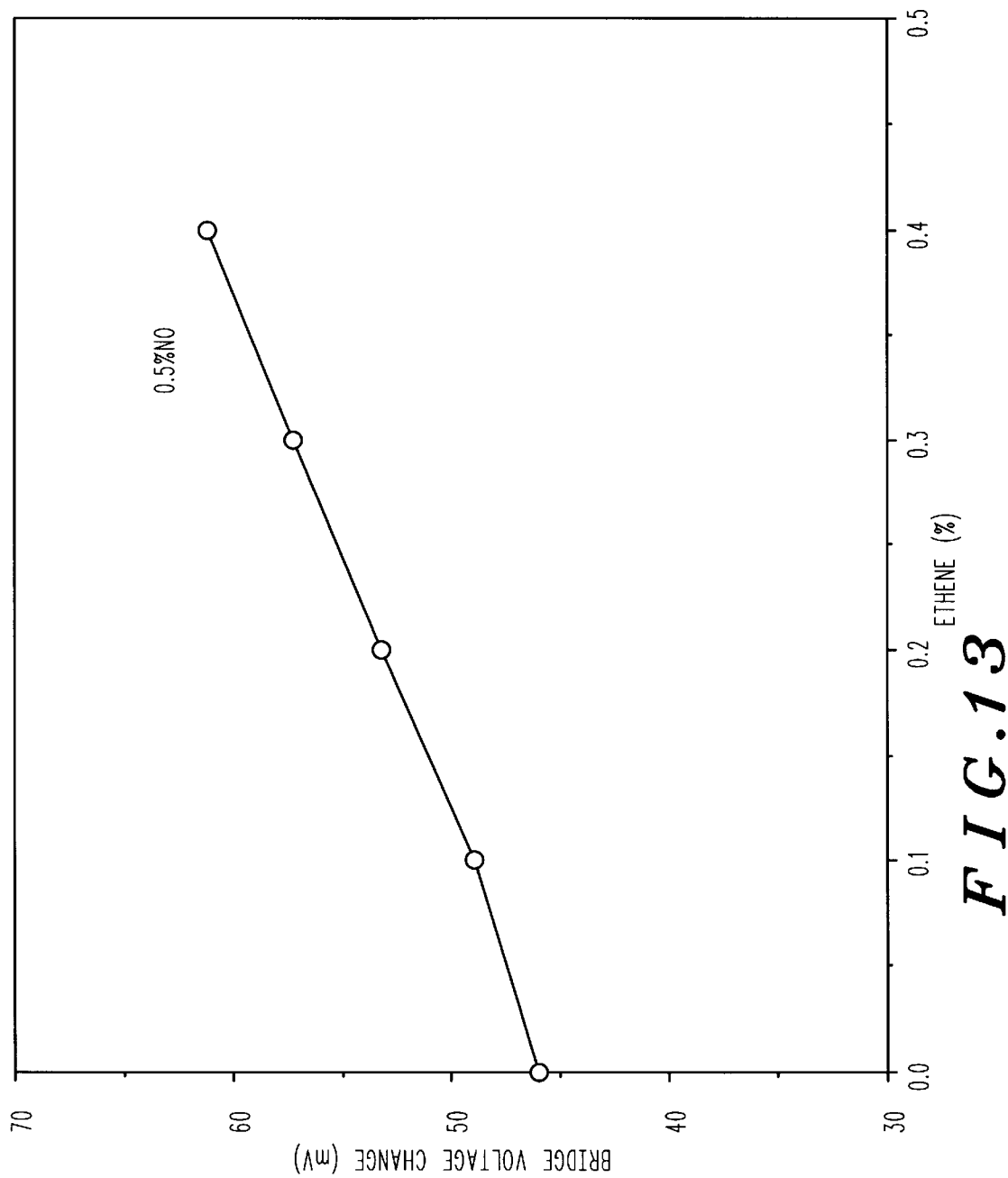
FIG. 13 is a graph showing measurement of ethene in the presence of nitric oxide (NO), where the nitric oxide (NO) concentration is held at 0.5% while ethene concentration is varied from 0% to 0.4%.
Figure 14:
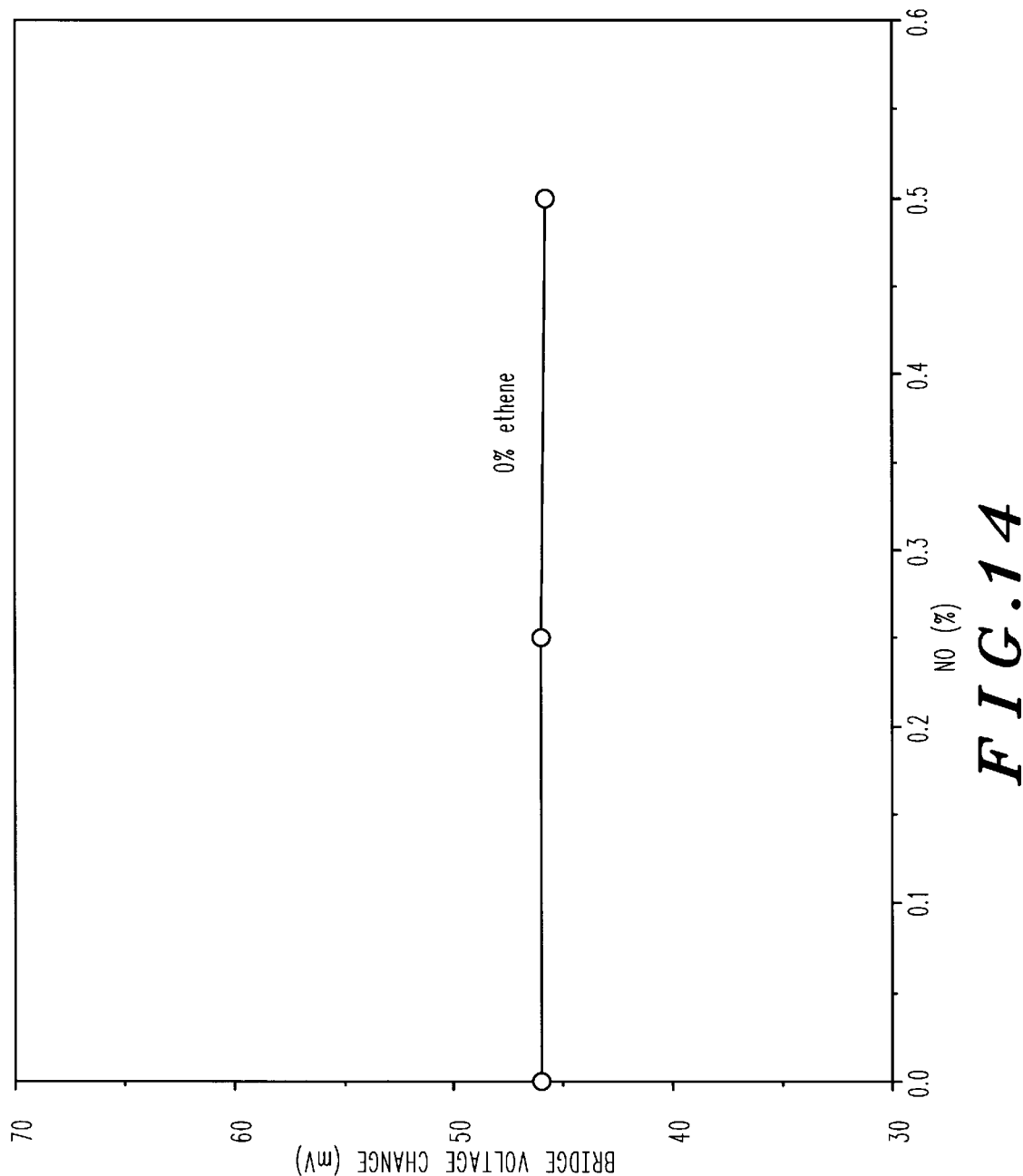
FIG. 14 is a graph illustrating measurement of ethene in the presence of nitric oxide (NO), where the nitric oxide (NO) concentration is varied from 0.0% to 0.5% while ethene is held constant.

FIG. 13 is a graph showing measurement of ethene in the presence of nitric oxide (NO), where the nitric oxide (NO) concentration is held at 0.5% while ethene concentration is varied from 0% to 0.4%. FIG. 14 is a graph illustrating measurement of ethene in the presence of nitric oxide (NO), where the nitric oxide (NO) concentration is varied from 0.0% to 0.5% while ethene is held constant. In conclusion, nitric oxide (NO) does not affect the ethene measurement.

In summary, the sensing element pair responded linearly to methylpropene (MP) in the concentration range of 400 to 2,500 PPM and to ethene in the range of 1,000 to 4,000 PPM. At concentrations below these levels, the results were not well reproduced because relatively large-sized (thermal mass) sensing elements were used.

Poisoning of the sensing element catalyst decreased the sensing element's response to combustible gases at a given operating temperature. Thus, an increase in the sensing element's operating voltage (or sensing element operating temperature) was required to produce a signal of the same magnitude. In other words, the poisoning shifted the signal curve to a higher temperature, as shown in FIGS. 3, 4, and 5. The increase (or the shift magnitude) depends on the level of poisoning and the microstructure of the sensors. According to scanning electron microscopy (SEM) and energy dispersive spectrometer (EDAX) analysis, the model VQ25 EEV sensing element had the catalyst distributed from the bead's surface to its center (Note: both model VQ25 EEV and model 62-0300 GasTech sensors are bead-type sensors), while the catalyst of the model 62-0300 GasTech bead-type sensing element was segregated near the surface as mentioned earlier.

The following discussion details effects of poisoning time and microstructure on the poisoning of the platinum (Pt) catalyst.

Figure 15:
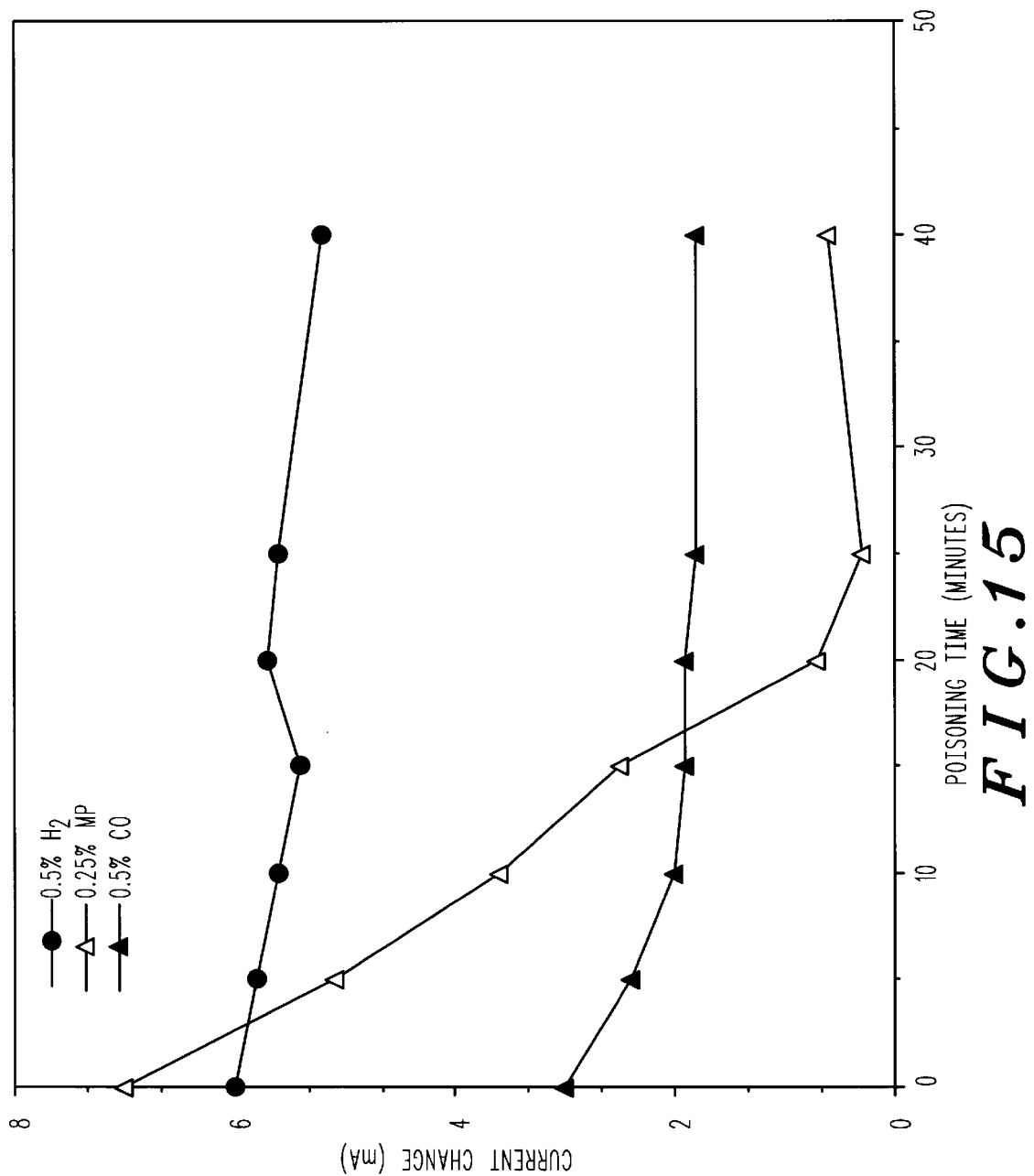
FIG. 15 is a graph showing measurement effect of poisoning at 430° C. on a first model VQ25 English Electric Valve sensor.
Figure 16:
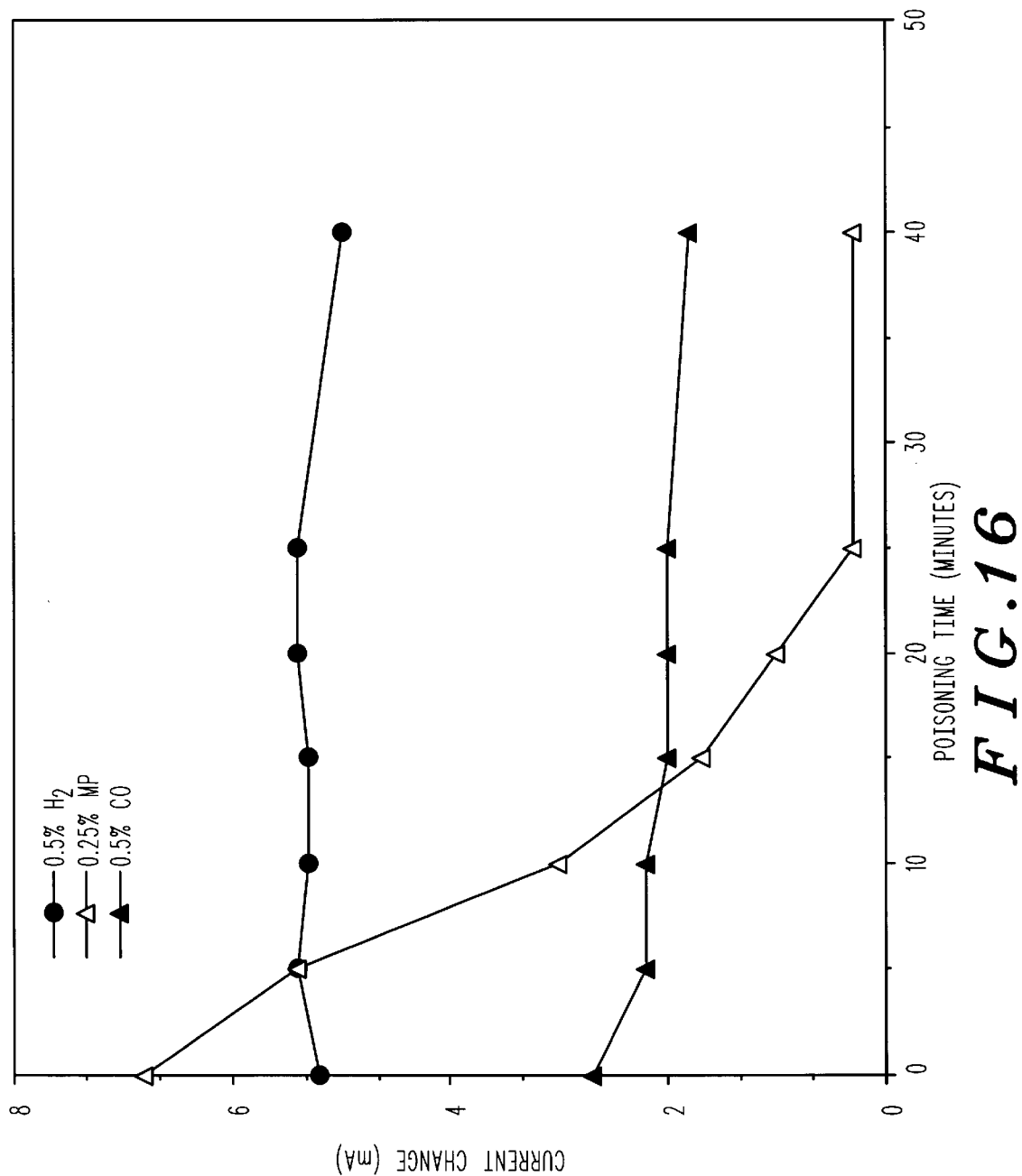
FIG. 16 is a graph illustrating measurement effect of poisoning at 430° C. on a second model VQ25 English Electric Valve sensor.
Figure 17:
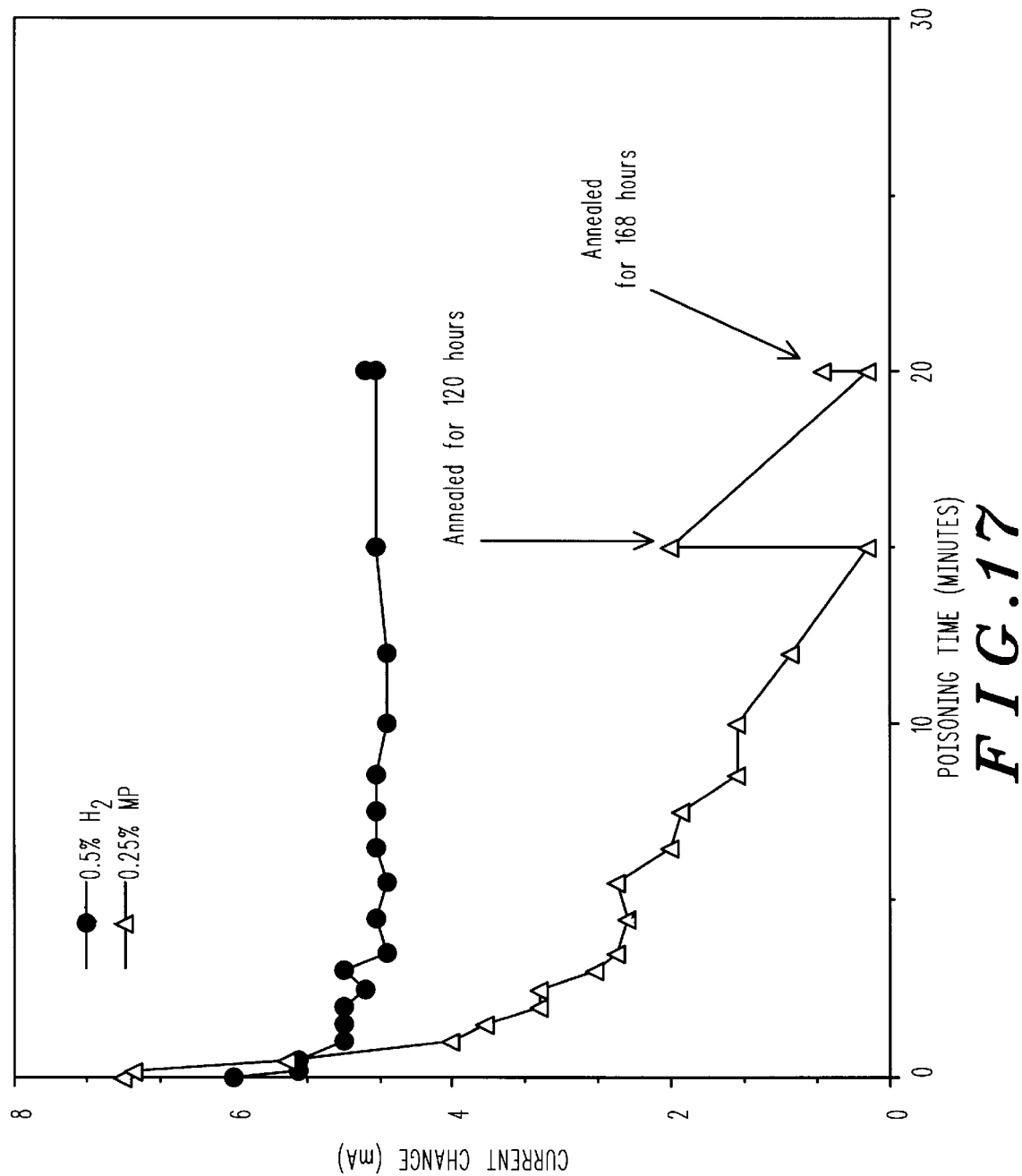
FIG. 17 is a graph showing measurement effect of poisoning at 430° C. on a third model VQ25 English Electric Valve sensor, including the effect of annealing on the poisoning.

The test results of three model VQ25 EEV sensing elements poisoned at 430° C. are given in FIGS. 15, 16, and 17 respectively, The three sensing elements were poisoned and tested at a temperature of 430° C. Signal was measured as a current change, where no Wheatstone bridge was used. Note that in FIGS. 15, 16, and 17, and later-described FIGS. 18–21, the Y-axis represents a current change measured through a single sensing element as the sensing element's resistance changes.

Figure 18:
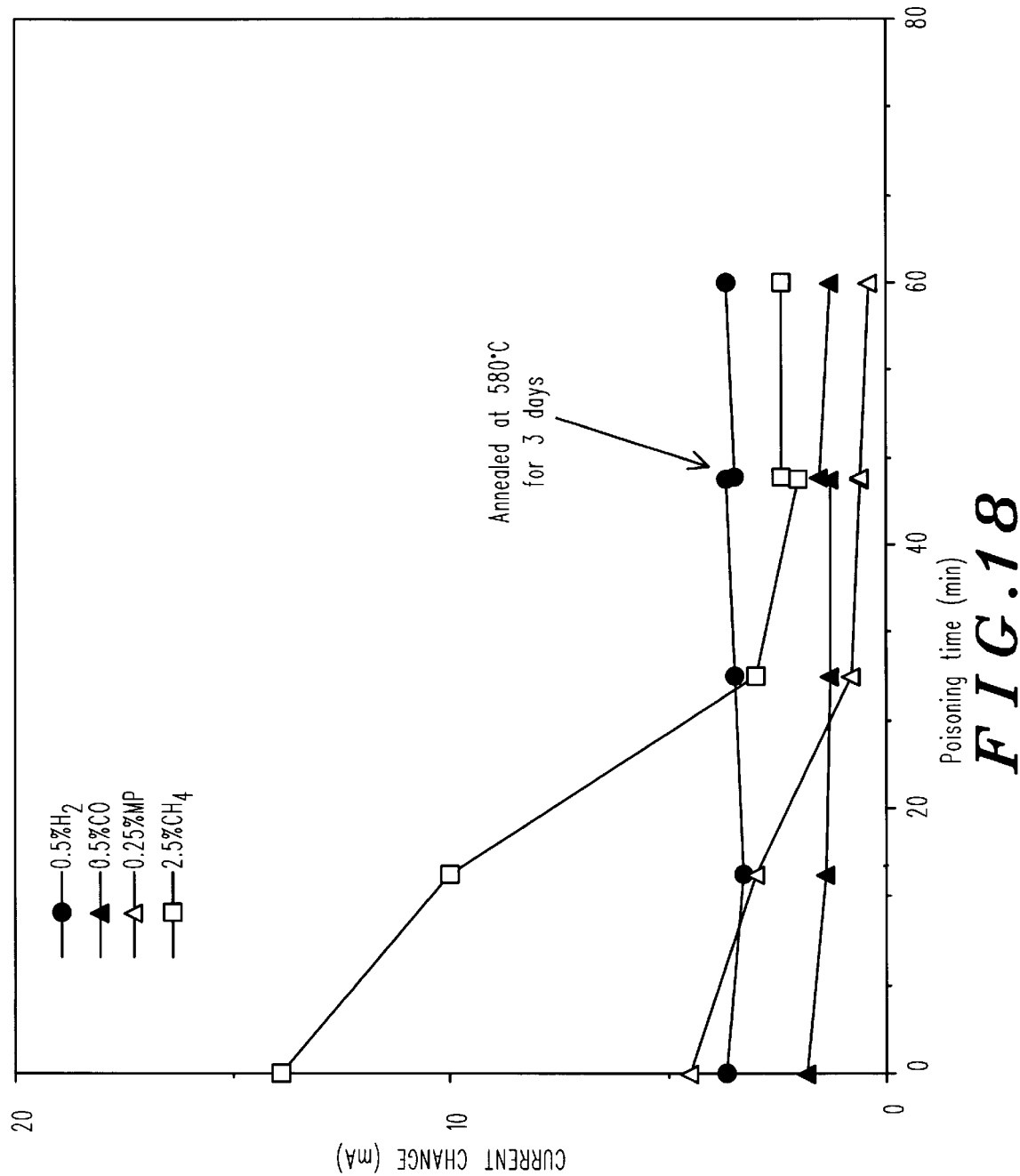
FIG. 18 is a graph illustrating test results of poisoning a sensing element at a temperature of 630° C.

As poisoning time increased, the sensitivity to methylpropene (MP) decreased considerably while the sensitivity to hydrogen ($H_2$) and carbon monoxide (CO) was less affected. FIG. 18 also indicates the effect of annealing on the poisoning. The sensitivity was recovered to some extent when the sensing element was annealed during the poisoning process (as shown at 15 minutes), but the recovery was considerably smaller when the poisoning was extended (as shown at 20 minutes). The term recovery here means the process of reversion to the sensing element's original behavior. The poisoning time is related to the level of poisoning. The poisoned sensing element lost almost 95% of the signal magnitude for methylpropene (MP) in 25 minutes, while the sensing element lost 15% or less of the signal magnitude for hydrogen ($H_2$) and 30% or less for carbon monoxide (CO) in the same period, as shown in FIG. 15 and FIG. 16. The sensitivities were then saturated, even though the level of poisoning increased.

When the sensing elements poisoned for 15 minutes were annealed for 120 hours at the same temperature as the poisoning temperature (430° C.), the sensitivity was recovered to some extent, as shown in FIG. 17. However, the recovery was considerably less when the poisoning was extended as shown at 20 minutes. The results confirmed that the sensing elements should be poisoned enough not to allow the sensitivity to be recovered.

Figure 19:
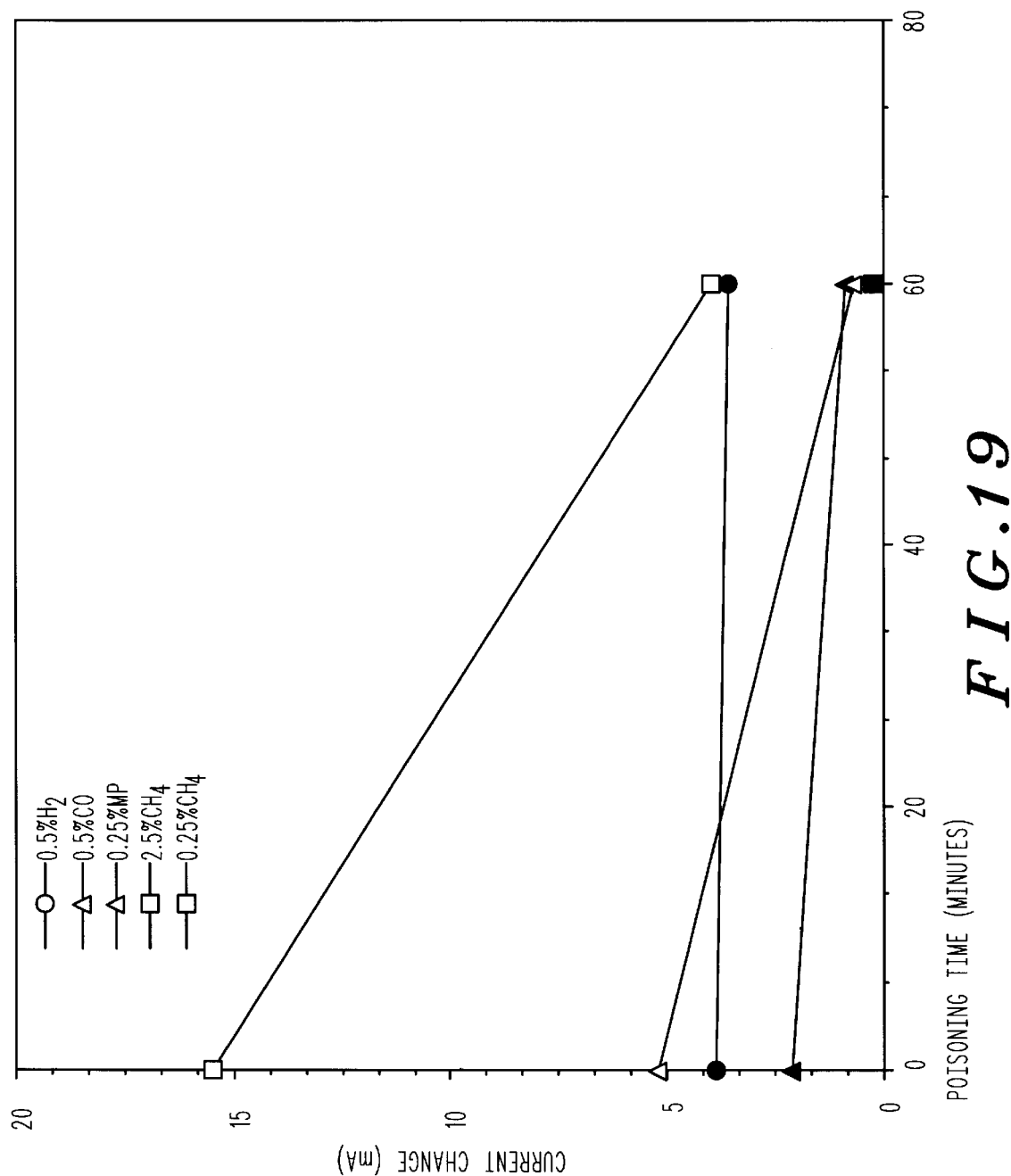
FIG. 19 is a graph showing test results of poisoning a sensing element at a temperature of 580° C.

FIG. 18 is a graph illustrating test results of poisoning a sensing element at a temperature of 630° C., and FIG. 19 is a graph showing test results of poisoning another sensing element at a temperature of 580° C. As with the last graphs (FIGS. 15, 16, and 17), the signals were measured as a change in current flowing through the sensing elements. After 45 minutes of accumulative poisoning of the sensing element used to generate the graph in FIG. 18, the sensing element was annealed at 580° C. for 3 days. The recovery was considerably small.

In FIG. 19 the other sensing element yielded a measurable signal, but at 0.25% methane ($CH_4$) which is more representative of engine exhaust gas, the signal was negligible.

After the above reported testing was complete, the model VQ25 EEV sensing element was poisoned for an additional 15 minutes, annealed for the same time, and then used to measure sensitivity to hydrogen ($H_2$), carbon monoxide (CO), methylpropene (MP), and methane ($CH_4$) as illustrated in FIG. 18. The just-prior-described process was repeated three additional times to result in the 60-minute total poisoning time. The model VQ25 EEV sensing element used to reproduce FIG. 19 was poisoned for 60 minutes and annealed for 60 minutes without interruption. The test results of the two sensing elements after the different 60 minute poisoning processes were the same, showing that the sensing elements remained stable using either continuous or discontinuous poisoning. Additionally, annealing at 580° C., for 3 days did not change the sensing element's response considerably, indicating that stable poisoning was attained.

Figure 20:
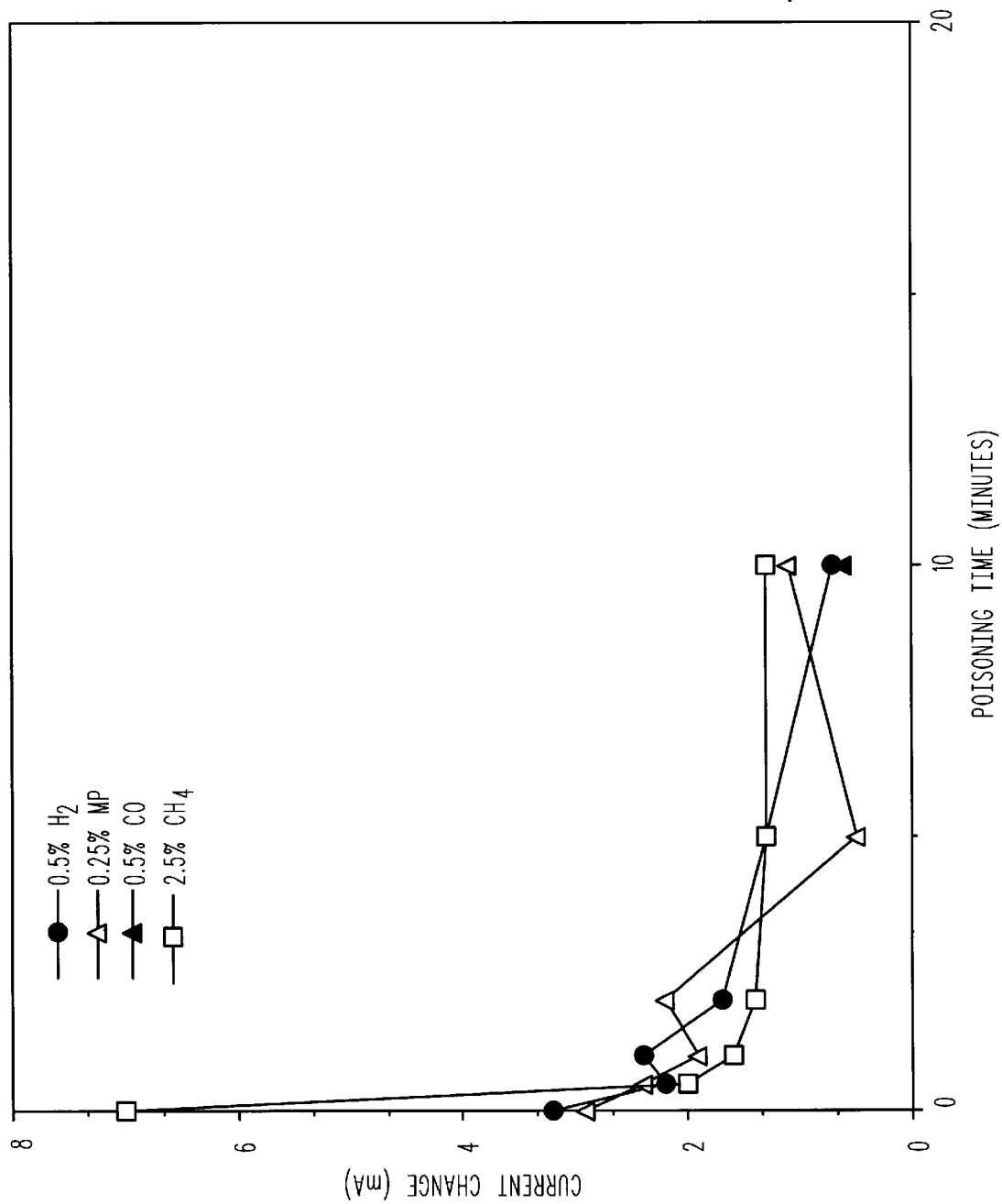
FIG. 20 is a graph illustrating poisoning results of an as-received catalytic GasTech model 62-0300 bead-type sensor.
Figure 21:
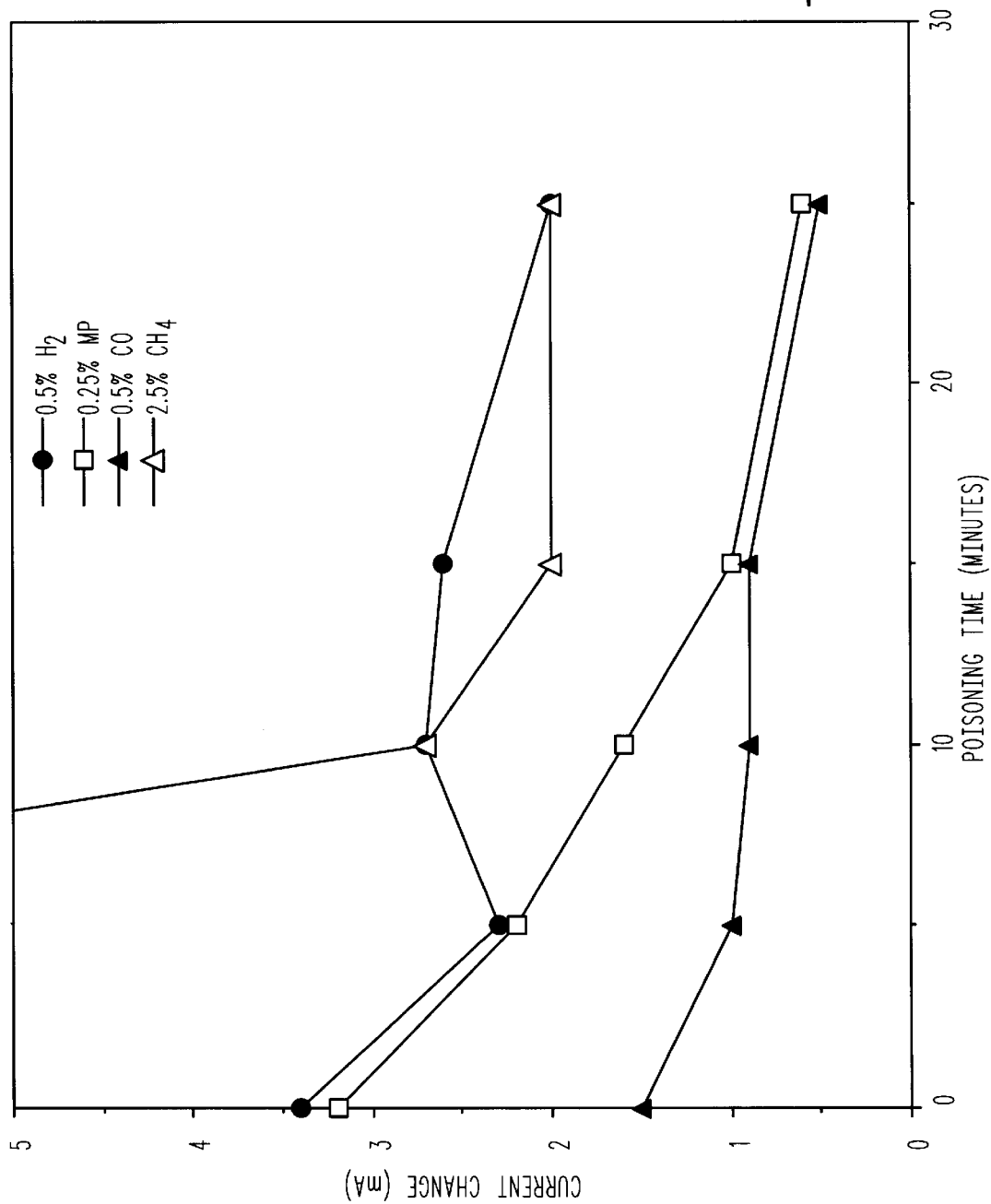
FIG. 21 is a graph illustrating poisoning results of a as-received catalytic GasTech model 62-0300 bead-type sensing element that is modified with an additional layer of a controllably poisonable catalyst prepared for controlled selective poisoning.

Next, poisoning of bead-type construction sensing elements will be considered, the results being shown in FIGS. 20 and 21. FIG. 20 shows the response of a model 62-0300 GasTech bead-type sensing element poisoned with 0.03% hexamethyldisilazane (HMDS), (which was 10 times more dilute than that used for the model VQ25 EEV sensing element). Approximately 60% of the signal magnitude was lost in 1 minute and no selectivity was given.

Note the curves in FIGS. 20 and 21 are not smooth because the sensing elements used to derived the graphs shown in were not sufficiently stabilized (before measurement). However, the general trend is consistent with other experiments.

When the model 62-0300 GasTech bead-type sensing element was coated with additional catalytic material (the controllably poisonable catalyst mentioned earlier consisting of silica power, alumina powder, and $Al(NO_3)_3 \cdot 9H_2O$ as catalyst carriers, $H_2PtCl_6$ as a catalyst), poisoning the additional catalytic material resulted in a decrease in the signal magnitude in the same way as with the model VQ25 EEV sensing element. This is illustrated in FIG. 21. The sensing element was selective as well.

Figure 22:
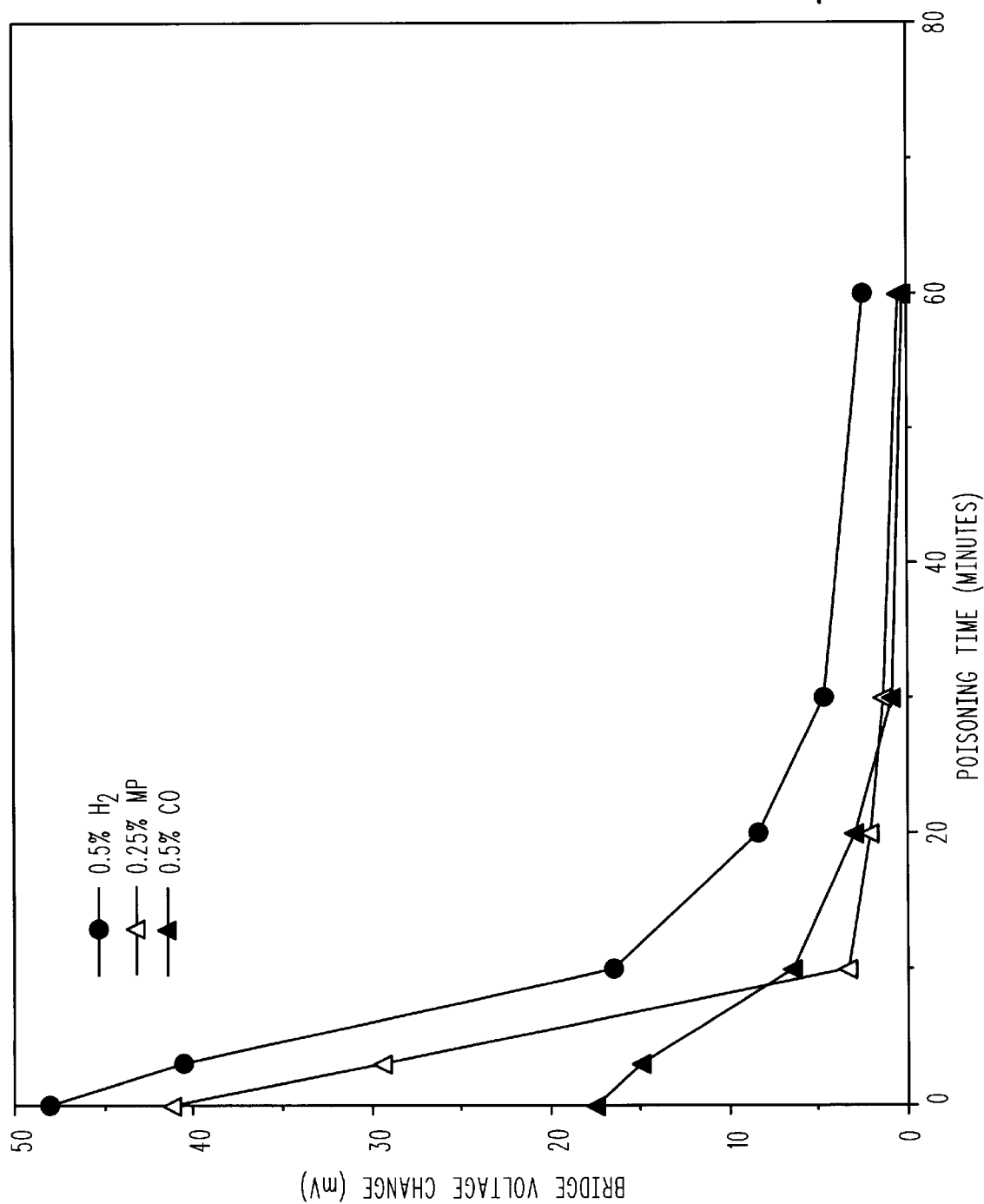
FIG. 22 shows a graph derived from an alternate sensing element constructed using an non-catalytic GasTech model 62-0300 sensing element coated with a thin film coating of the controllably poisonable catalyst.

Next, bead-type sensing elements were constructed using a non-catalytic (the element fabrication process was stopped prior to addition of the catalytic material found on a complete sensing element) GasTech model 62-0300 sensing element. One device was coated with a thin film coating of the controllably poisonable catalyst, and the other device was coated with a thick film coating of the controllably poisonable catalyst. The sensor elements' responses are shown in FIGS. 22 and 23 respectively.

The results of the poisoning clearly show that the thick catalyst coating can make the poisoned sensing element selective, as shown in FIG. 23. The same conclusion can be made for the model VQ25 EEV sensing element, which has diffused catalyst across the sensor bead. The better selectivity of the model VQ25 EEV sensing element, shown when FIGS. 15–17 and 23 are compared, is due to the gas-permeation characteristics of the bead structure of the model VQ25 EEV sensing element, through which smaller molecules such as hydrogen ($H_2$) and carbon monoxide (CO) can diffuse to the center, which is not poisoned.

Model VQ25 EEV and model 62-0300 GasTech sensing elements, as well as modified model 62-0300 GasTech bead-type sensing elements, were poisoned by hexamethyldisilazane (HMDS) and the selectivity was evaluated. Poisoning of the model VQ25 EEV sensing element, which was stabilized by controlling the level of poisoning, was reproducible from sensing element to sensing element. The onset temperature of combustion (or voltage applied to the sensing element) of combustible gases increased as the level of poisoning increased. The magnitude of increase was different for the gases of interest, the order of increase being with hydrogen ($H_2$), carbon monoxide (CO), non-methane hydrocarbons methylpropene (MP), ethene, and methane ($CH_4$). Pairing and operating of two sensing elements, lightly poisoned and heavily poisoned, selectively measured the non-methane hydrocarbons in the presence of hydrogen ($H_2$), carbon monoxide (CO), and methane ($CH_4$). The signals from hydrogen ($H_2$) and carbon monoxide (CO) were canceled, and the signal from methane ($CH_4$) was too small to measure (or was canceled).

The selectivity of poisoned sensing elements depended on several factors. The microstructure of the sensing element bead is important. According to SEM and EDAX analysis, the catalyst of the model VQ25 EEV sensing element was distributed from the bead surface to the center of the bead, but the model 62-0300 GasTech sensing element consists of bare alumina bead body and a catalyst segregated on the bead surface as mentioned earlier. The gas-permeation characteristics of the bead structure of the model 62-0300 GasTech bead-type sensing element were different to those of the model VQ25 EEV sensing element, so the model 62-0300 GasTech bead-type sensing element was more gas-permeable. Such differences caused the catalyst in the model 62-0300 GasTech sensing element to be vulnerable to hexamethyldisilazane (HMDS) gas and thus to quickly lose its sensitivity in a nonselective manner. When the model 62-0300 GasTech sensing bead was coated with a controllably poisonable catalyst made to form a thick catalyst layer, the signal magnitude gradually decreased with poisoning and appeared selective among hydrogen ($H_2$), carbon monoxide (CO), and methylpropene (MP). The same trend was observed when model 62-0300 GasTech reference beads made of alumina were coated with different thicknesses of the controllably poisonable catalyst and then tested.

Selectivity also depends on materials and construction. The model VQ25 EEV sensor consisted of $Al_2O_3$ and $SiO_2$ as major carrier materials, while model 62-0300 GasTech bead-type sensors had $Al_2O_3$. However, the actual materials are not deciding factors in selective poisoning, but are supplemental to the role of the microstructure.

The sensor signal obtained by the subtraction method was linear to the concentrations of non-methane hydrocarbons—methylpropene (MP) and ethene. Interference with hydrogen ($H_2$) and carbon monoxide (CO) was not observed, but accurate measurement of the hydrocarbons requires better matching of the sensor pair, or use of suitable calibration techniques to account for non-identical responses of the two sensing elements. The coexistence of methane ($CH_4$), carbon dioxide ($CO_2$), nitric oxide (NO), and water ($H_2O$) vapor did not affect the hydrocarbon measurement. We observed that the measurement was not reproducible at low concentrations because of the sensing elements' large size, and hold that miniaturizing the sensor can solve this problem. Both pair matching and miniaturization can be achieved by batch fabrication of the sensors.

Good linearity in the measurement of hydrocarbons was obtained in the concentration range for which current large sensing elements are useful (for example, 400 to 2.500 PPM for methylpropene (MP) and 1,000 to 4,000 PPM for ethene).

In conclusion, the structure presented here clearly demonstrates the feasibility of measuring hydrocarbons in the presence of the interfering gases in the exhaust particularly hydrogen ($H_2$) through the use of modified (or poisoned) noble metal based sensing elements. Further optimization of the catalyst carrier material (e.g., grain size, size distribution) and miniaturization of the sensor will only improve the hydrocarbon sensor's accuracy.

What is claimed is:

1. A modified noble metal catalyst based calorimetric sensor for sensing non-methane hydrocarbons in an automotive exhaust gas stream comprising:
    a first sensing element having an output for providing a signal indicative of a concentration of indicative of non-methane hydrocarbons, hydrogen ($H_2$), and carbon monoxide (CO);
    a compensating sensing element having an output for providing a compensating signal indicative of a concentration of hydrogen ($H_2$) and carbon monoxide (CO); and
    a circuit for combining the signal and the compensating signal, and for providing a combined signal indicative of a measure of non-methane hydrocarbons in the automotive exhaust gas stream.

2. A sensor in accordance with claim 1 wherein the first sensing element comprises:
    a substrate having a body portion;
    a poisoned noble metal catalytic material dispersed through the body portion of the substrate; and
    a temperature measurement device positioned thermally coupled to the poisoned noble metal catalytic material, the temperature measurement device having output terminals for providing a signal having a magnitude indicative of a temperature proximate the thermal coupling.

3. A sensor in accordance with claim 2 wherein a noble metal portion of the poisoned noble metal catalytic material comprises a material selected from a group consisting of platinum (Pt), palladium (Pd), and rhodium (Rh).

4. A sensor in accordance with claim 3 wherein the circuit for combining comprises a Wheatstone bridge measurement circuit.

5. A sensor in accordance with claim 4 wherein the sensor is disposed to operate at a temperature above 200° C.

6. A sensor in accordance with claim 1 wherein the compensating sensing element comprises:
    a substrate having a body portion;
    a poisoned noble metal catalytic material dispersed through the body portion of the substrate; and
    a temperature measurement device positioned thermally coupled to the poisoned noble metal catalytic material, the temperature measurement device having output terminals for providing a signal having a magnitude indicative of a temperature proximate the thermal coupling.

7. A sensor in accordance with claim 6 wherein a noble metal portion of the poisoned noble metal catalytic material comprises a material selected from a group consisting of platinum (Pt), palladium (Pd), and rhodium (Rh).

8. A sensor in accordance with claim 7 wherein the circuit for combining comprises a Wheatstone bridge measurement circuit.

9. A sensor in accordance with claim 8 wherein the sensor is disposed to operate at a temperature above 200° C.

10. A modified noble metal catalyst based calorimetric sensor for sensing non-methane hydrocarbons in an automotive exhaust gas stream comprising:
    a first sensing element having an output for providing a signal indicative of a concentration of indicative of non-methane hydrocarbons, hydrogen ($H_2$), and carbon monoxide (CO), wherein first sensing element is constructed with a heavily poisoned noble metal catalytic material dispersed through a body portion of the first sensing element, and a first temperature measurement device for providing a signal having a magnitude indicative of a first temperature proximate the heavily poisoned noble metal catalytic material;
    a compensating sensing element having an output for providing a compensating signal indicative of a concentration of hydrogen ($H_2$) and carbon monoxide (CO), wherein the compensating sensing element is constructed with a lightly poisoned noble metal catalytic material dispersed through a body portion of the compensating sensing element, and a compensating temperature measurement device for providing a compensating signal having a magnitude indicative of a compensating temperature proximate the lightly poisoned noble metal catalytic material, wherein a poisoning concentration of the heavily poisoned noble metal catalytic material is greater than a poisoning concentration of the lightly poisoned noble metal catalytic material; and
    a circuit for combining the signal and the compensating signal, and for providing a combined signal indicative of a measure of non-methane hydrocarbons in the automotive exhaust gas stream.

11. A sensor in accordance with claim 10 wherein the sensor is controlled to operate at a temperature above 200° C.

12. A method for detecting non-methane hydrocarbons in an automotive exhaust gas stream comprising the steps of:
    exposing a heavily poisoned noble metal catalyst to the automotive exhaust gas stream and deriving a signal indicative of a temperature proximate the heavily poisoned noble metal catalyst;
    exposing a lightly poisoned noble metal catalyst to the automotive exhaust gas stream and deriving a compensating signal indicative of a temperature proximate the lightly poisoned noble metal catalyst; and
    combining the signal and the compensating signal and providing a signal indicative of a concentration of non-methane hydrocarbons in the automotive exhaust gas stream dependent thereon.

* * * * *